(12) United States Patent
Tiwari-Pandey et al.

(10) Patent No.: US 11,147,805 B2
(45) Date of Patent: Oct. 19, 2021

(54) CANNABINOID RECEPTOR AGONISTS AND SERINE HYDROLASE ENZYME INHIBITOR BASED ANXIOLYTIC THERAPEUTIC PRODUCT

(71) Applicant: Medipure Pharmaceuticals Inc., North Vancouver (CA)

(72) Inventors: Rashmi Tiwari-Pandey, Surrey (CA); Rakshit Devappa Kodekalra, Burnaby (CA); Nihar R. Pandey, Surrey (CA)

(73) Assignee: Medipure Pharmaceuticals Inc., North Vancouver (CA)

( * ) Notice: Subject to any disclaimer, the term of this patent is extended or adjusted under 35 U.S.C. 154(b) by 0 days.

(21) Appl. No.: 16/270,389

(22) Filed: Feb. 7, 2019

(65) Prior Publication Data

US 2020/0253947 A1   Aug. 13, 2020

(51) Int. Cl.
   *A61K 31/4525*    (2006.01)
   *A61K 31/05*      (2006.01)
   *A61P 25/22*      (2006.01)

(52) U.S. Cl.
   CPC .......... *A61K 31/4525* (2013.01); *A61K 31/05* (2013.01); *A61P 25/22* (2018.01)

(58) Field of Classification Search
   None
   See application file for complete search history.

(56) References Cited

U.S. PATENT DOCUMENTS

| | | | |
|---|---|---|---|
| 7,700,368 B2 | 4/2010 | Flockhart et al. | |
| 2019/0029993 A1* | 1/2019 | Postrel | A61K 36/82 |

FOREIGN PATENT DOCUMENTS

| | | |
|---|---|---|
| WO | 02/32420 A1 | 4/2002 |
| WO | 02/064109 A2 | 8/2002 |
| WO | 2004/026802 A1 | 4/2004 |
| WO | 2006/116773 A2 | 11/2006 |
| WO | 2009/052320 A1 | 4/2009 |
| WO | 2010/056309 A2 | 5/2010 |
| WO | 2013/098402 A1 | 7/2013 |
| WO | 2014/100231 A1 | 6/2014 |
| WO | 2014/127458 A1 | 8/2014 |
| WO | 2015/065179 A1 | 5/2015 |
| WO | 2018/109471 A1 | 6/2018 |

OTHER PUBLICATIONS

Pertwee, Handbook of Cannabis, 2014, Oxford: Oxford University Press, 784 (39 pages).
Huestis, "Human Cannabinoid Pharmacokinetics", Chem Biodivers, 4(8):1770-1804, 2007.
Zuardi et al., "Cannabidiol: from an inactive cannabinoid to a drug with wide spectrum of action", Brazilian Journal of Psychiatry, 30(3):271-280, 2008.
Zuardi et al., "Effects of ipsapirone and cannabidiol on human experimental anxiety", Journal of Psychopharmacology, 7(1 Suppl):82-88, 1993.
Cunha et al., "Chronic Administration of Cannabidiol to Healthy Volunteers and Epileptic Patients", Pharmacology, 21(3):175-185, 1980.
Consroe et al., Controlled Clinical Tril of Cannabidiol in Huntington's Disease, Pharmacology Biochemistry & Behavior, 40(3):701-708, 1991.
Karlsson et al., "cDNA Cloning, Tissue Distribution, and Identification of the Catalytic Triad of Monoglyceride Lipase", Journal of Biological Chemistry, 272(43):27218-27223, 1997.
Repetto et al., "Separation of cannabinoids", United Nations Office on Drugs and Crime (UNODC), Bulletin on Narcotics, 1976 Issue 4, 5 pages.
Narayanaswami et al., "Stability of *Cannabis sativa* L. samples and their extracts, on prolonged storage in Delhi", United Nations Office on Drugs and Crime (UNODC), Bulletin on Narcotics, 1978 Issue 4, 12 pages.
Smith et al., "The decomposition of acidic and neutral cannabinoids in organic solvents", Journal of Pharmacy and Pharmacology, 29(1):286-290, 1977.
Aubin, "Purification of Cannabidiol from Hemp Oil Using the Prep 150 LC System", Water Application Notes, in http://www.waters.com/waters/webassets, 2015, pp. 1-5.
Bachovchin and Cravatt, "The Pharmacological Landscape and Therapeutic Potential of Serine Hydrolases", Nat Rev Drug Discov., 11(1):52-68, 2012.
Chou and Martin, CompuSyn for drug combinations: PC software and user's guide. A Computer Program for Quantitation of Synergism and Antagonism in Drug Combinations, and the Determination of IC50 and ED50 and LD50 Values, CompuSyn, PD Science, 2005, Paramus, NJ, 7652-1754, 68 pages.
Fu et al., "Drug combination in vivo combination index method: Taxotere and T607 against colon carcinoma HCT-116 xenograft tumor in nude mice". Synergy, 3(3):15-30, 2016.
Tiwari et al., "Phytochemical screening and Extraction: A Review", Internationale Pharmaceutica Sciencia, 1(1):100-106, 2011.
Bedse et al. Therapeutic cendocannobinoid augmentation for mood and anxiety disorders: comparative profiling of FAAH, MAGL and dual inhibitors. Translational psychiatry 2018, 8(1):92.
Blessing, et al. Cannabidiol as a Potential Treatment for Anxiety Disorders. Neurotherapeutics 2015, 12(4):825-36.
Gennaro, Remington's Pharmaceutical Sciences 18th Edition, 1990, Mack Publishing Co., Easton, PA, Chapters 75-92 (284 pages).
Sciolino et al. Enhancement of endocannabinoid signaling with JZL184, an inhibitor of the 2-arachidonoylglycerol hydrolyzing enzyme monoacylglycerol lipase, produces anxiolytic effcts under conditions of high environmental averiveness in rats. Pharmacological Research 2011, 64(3):226-234.

* cited by examiner

*Primary Examiner* — Samantha L Shterengarts
(74) *Attorney, Agent, or Firm* — Honigman LLP; Fernando Alberdi; Jonathan P. O'Brien

(57) ABSTRACT

Provided herein are formulations for treating affective mood disorders. The formulations comprise one or more than one CB receptor agonist and one or more than one serine hydrolase enzyme inhibitor.

21 Claims, 3 Drawing Sheets

CANNABINOID RECEPTOR AGONISTS AND SERINE HYDROLASE ENZYME INHIBITOR BASED ANXIOLYTIC THERAPEUTIC PRODUCT

FIELD OF INVENTION

This disclosure relates to formulations for treating mood disorders. Specifically, the present disclosure is related to formulations that combine one or more than one cannabinoid receptor agonist and one or more than one serine hydrolase enzyme inhibitor to treat mood disorders.

BACKGROUND OF THE INVENTION

Anxiety stems from and perpetuates dysregulation of neurobiological systems, but the exact mechanisms of anxiety disorders are still only partially understood. Low levels of gamma-aminobutyric acid (GABA), a neurotransmitter that reduces activity in the central nervous system, contribute to anxiety. A number of anxiolytics achieve their effect by modulating the GABA receptors.

The GABA receptors are a class of receptors that respond to GABA, which is the chief inhibitory neurotransmitter in the mature vertebrate central nervous system. There are two classes of GABA receptors: $GABA_A$ (or GABA(A)) and $GABA_B$ (or GABA(B)). $GABA_A$ receptors are ligand-gated ion channels (also known as ionotropic receptors), whereas $GABA_B$ receptors are G protein-coupled receptors (also known as metabotropic receptors).

All $GABA_A$ receptors contain an ion channel that conducts chloride ions across neuronal cell membranes and two binding sites for GABA, while a subset of $GABA_A$ receptor complexes also contain a single binding site for benzodiazepines. Binding of benzodiazepines to this receptor complex does not alter binding of GABA. Unlike other positive allosteric modulators that increases ligand binding, benzodiazepine binding acts as a positive allosteric modulator by increasing the total conduction of chloride ions across the neuronal cell membrane when GABA is already bound to its receptor. Therefore, benzodiazepines enhance the effect of GABA at the $GABA_A$ receptor, resulting in sedative, hypnotic (sleep-inducing), anxiolytic (anti-anxiety), anticonvulsant, and muscle relaxant properties.

While benzodiazepine products have been in the market to treat anxiety and associated mood disorders for some time, their use by many patients is poorly tolerated and include side effects such as: drowsiness, dizziness, decreased alertness and concentration, decreased libido, erection problems, depression, disinhibition, nausea, changes in appetite, blurred vision, confusion, euphoria, depersonalization, nightmares, liver toxicity, aggression, violence, impulsivity, irritability, suicidal behavior, seizures in people with epilepsy, anterograde amnesia, confusion, ataxia, hangover effects, falls, benzodiazepine dependence, and benzodiazepine withdrawal syndrome.

Cannabis has been used as an anxiolytic, however the use has been limited to dry plant product which is smoked or a crude or standardized extract containing a mixture of uncharacterized phytochemical bioactives, including psychoactive cannabinoids such as tetrahydrocannabinol (THC) at concentrations which may produce negative side effects such as decrease in short-term memory, dry mouth, impaired motor skills, reddening of the eyes, increased heart rate, increased appetite and consumption of food, lowered blood pressure, impairment of short-term and working memory, reduced psychomotor coordination and concentration, and an increased risk of developing schizophrenia with adolescent use.

Cannabinoids are a class of diverse chemical compounds that act on cannabinoid receptors on cells that repress neurotransmitter release in the brain. Ligands for these receptor proteins include the endocannabinoids (produced naturally in the body by humans and animals), the phytocannabinoids (found in cannabis and some other plants), and synthetic cannabinoids (manufactured artificially). Over 100 different cannabinoids have been isolated from cannabis, exhibiting varied effects [1]. The most notable cannabinoid is the phytocannabinoid tetrahydrocannabinol (THC), the primary psychoactive compound of cannabis mentioned above. Cannabidiol (CBD), one major non-psychotomimetic compound of the plant, shows psychological effects substantially different from those of THC, by having anxiolytic effects both in humans and in animals.

Oral administration of CBD to healthy volunteers has been shown to attenuate the anxiogenic effect of THC and does not seem to involve any pharmacokinetic interactions [2]. In animal studies, CBD has similar effects to anxiolytic drugs in different paradigms including conditioned emotional response, the Vogel conflict test, and the elevated plus-maze test [3]. In human studies, the anxiolytic effects of CBD have been elicited in subjects submitted to the Simulation Public Speaking Test (SPST) [4]. No signs of toxicity or serious side effects have been observed following chronic administration of cannabidiol to healthy volunteers [5], even in large acute doses of 700 mg/day [6].

There are currently no cannabinoid prescription products on the market to treat mood disorders, particularly anxiety.

The endocannabinoid system (ECS) is a group of endogenous cannabinoid receptors located in the mammalian brain and throughout the central and peripheral nervous systems, consisting of neuromodulatory lipids and their receptors. The ECS is involved in a variety of physiological processes including appetite, pain-sensation, mood, and memory, and in mediating the psychoactive effects of cannabis. Two primary endocannabinoid receptors have been identified: CB1 and CB2. CB1 receptors are found predominantly in the brain and nervous system, as well as in peripheral organs and tissues, and are the main molecular target of the endocannabinoid ligand Anandamide (AEA), as well as its mimetic phytocannabinoid, delta 9-tetrahydrocannabinol (THC). Cannabinoids such as psychoactive THC activate CB1 and CB2 receptors, but mainly exhibits its neurobehavioural effects by interacting with CB1 receptors. CB1 agonism produces medicinally useful activities, such as analgesia, but also a number of undesirable side effects, including locomotor and cognitive impairments, as well as abuse liability. To date, it has proved difficult to uncouple these beneficial and untoward properties, thus limiting the therapeutic utility of direct CB1 agonists.

One other main endocannabinoid is 2-Arachidonoylglycerol (2-AG) which is active at both cannabinoid receptors, along with its own mimetic phytocannabinoid, CBD. 2-AG and CBD are involved in the regulation of appetite, immune system functions and pain management.

Endogenous cannabinoids (i.e., endocannabinoids), such as AEA and 2-AG, are produced throughout the limbic system and other brain regions associated with emotionality and are believed to modulate behavioral responses to stress-related conditions. Inhibition of AEA and 2-AG degradation can increase the endogenous pool of AEA and 2-AG thereby stimulating the endocannabinoid system resulting in diverse physiological effects. AEA and 2-AG are rapidly metabolized by the respective enzymes fatty acid amide hydrolase (FAAH) and monoacylglycerol lipase (MAGL). Accordingly, inhibition of each enzyme increases brain levels of the appropriate endogenous cannabinoid. Therefore, the modulation of endocannabinoid system can result in diverse physiological processes including, inflammation, cognition, feeding, neurodegeneration etc.

MAGL is a key enzyme in the hydrolysis of endocannabinoid 2-arachidonoylglycerol (2-AG). It converts monoacylglycerols to the free fatty acid and glycerol. Inhibition of MAGL increases the endogenous 2-AG pool resulting in increased stimulation of endocannabinoid system, which subsequently can exert anti-anxiety effects. MAGL is the main enzyme involved in the 2-AG hydrolysis to arachidonic acid (AA) and glycerol in the brain.

MAGL, a 33-kDa membrane-associated protein with 303 amino acid residues, is classified as a member of $\alpha/\beta$-hydrolase family. MAGL active site contains the classical catalytic triad (Ser122-His269-Asp239) and the lipase motif GXSXG typical of serine hydrolases. The nucleophilic Ser122 is activated by the Asp239 and the His269 residues [7]. Several natural and synthetic MAGL inhibitors have been identified that have been shown to exhibit antianxiety activity.

SUMMARY OF THE INVENTION

This summary of the invention does not necessarily describe all features of the invention.

The present discloser relates to formulations for treating an affective disorder comprising in combination an effective amount of one or more than one CB receptor agonist and an effective amount of one or more than one serine hydrolase enzyme inhibitor.

The combination of the one or more than one CB receptor agonist and one or more than one serine hydrolase enzyme inhibitor, may be a synergistic combination.

In the formulation as described herewith, the one or more than one CB receptor agonist and the one or more than one serine hydrolase enzyme inhibitor may be present in an effective amount to improve the therapeutic outcome and reduced dosage of the one or more than one CB receptor agonist and/or one or more than one serine hydrolase enzyme inhibitor.

The one or more than one CB receptor agonist may be one or more than one cannabinoid. The one or more than one serine hydrolase enzyme inhibitor may be one or more than one monoacylglycerol lipase (MAGL) inhibitor. The one or more than one cannabinoid may be an anxiolytic cannabinoid. In one aspect the one or more than one cannabinoid may be cannabidiol (CBD). In another aspect the one or more than one MAGL inhibitor may be KML29, a KML29 derivative, JZL184, a JZL184 derivative or a combination thereof. The effective amount of CBD in the formulation may be between 1 mg and 1000 mg or any amount there between. The effective amount of the one or more MAGL inhibitor is between 1 mg and 1000 mg or any amount there between.

The MAGL inhibitor may be KML29, a KML29 derivative, JZL184, a JZL184 derivative or a combination thereof. The effective amount of KML29 or its derivative may be between about 1 to about 1000 mg. The effective amount of JZL184 or its derivative may be between about 1 to about 1000 mg. In one aspect the effective amount of KML29 or a KML29 derivative may be 3 mg/kg, 10 mg/kg, 15 mg/kg, 20 mg/kg, 25 mg/kg or 30 mg/kg. In one aspect the effective amount of JZL184 or a JZL184 derivative may be 3 mg/kg, 10 mg/kg, 15 mg/kg, 20 mg/kg, 25 mg/kg or 30 mg/kg. In another aspect the effective amount of CBD may be 0.1 mg/kg, 0.5 mg/kg, 1 mg/kg, 5 mg/kg or 10 mg/kg.

It is further provided a pharmaceutical preparations for treating anxiety comprising the formulation as described above and a physiologically acceptable surface-active agents, carriers, diluents, excipients, smoothing agents, suspension agents, film forming substances, and coating assistants, or a combination thereof.

The formulation may be used to treat an affective disorder such as anxiety. Anxiety may comprise generalized anxiety disorder, phobias, panic disorder, panic attacks, obsessive-compulsive disorder, post-traumatic stress disorder (PTSD), separation anxiety disorder, situational anxiety disorder, stress or a combination thereof.

Therefore, the present discloser also relates to a method of treating an affective disorder by administering to a subject in need thereof the formulation or pharmaceutical preparation as described above. The treating may comprise treating over an extended treatment period, wherein the extended treatment period may be at least 21 days. The treatment may further comprise a protracted treatment period. The protracted treatment period may be between about 1 to about 21 days, or any amount of days therebetween.

In the method, the formulation may be administered transmucosal, oral, transdermal, intraperitoneal routes. The transmucosal administration may be sublingual, buccal, nasal, ocular, vaginal, and/or rectal mucosae. The formulation may be delivered in an appropriate aerosol, liquid, gel, or tablet/solid drug carrier with drug stabilizers/additives.

The affective disorder treated by the method may include anxiety. The anxiety treated by the method may comprise generalized anxiety disorder, phobias, panic disorder, panic attacks, obsessive-compulsive disorder, post-traumatic stress disorder (PTSD), separation anxiety disorder, situational anxiety disorder, stress or a combination thereof.

This summary of the invention does not necessarily describe all features of the invention.

BRIEF DESCRIPTION OF THE DRAWINGS

These and other features of the description will become more apparent from the following description in which reference is made to the appended drawings wherein.

DETAILED DESCRIPTION

Figure 1:
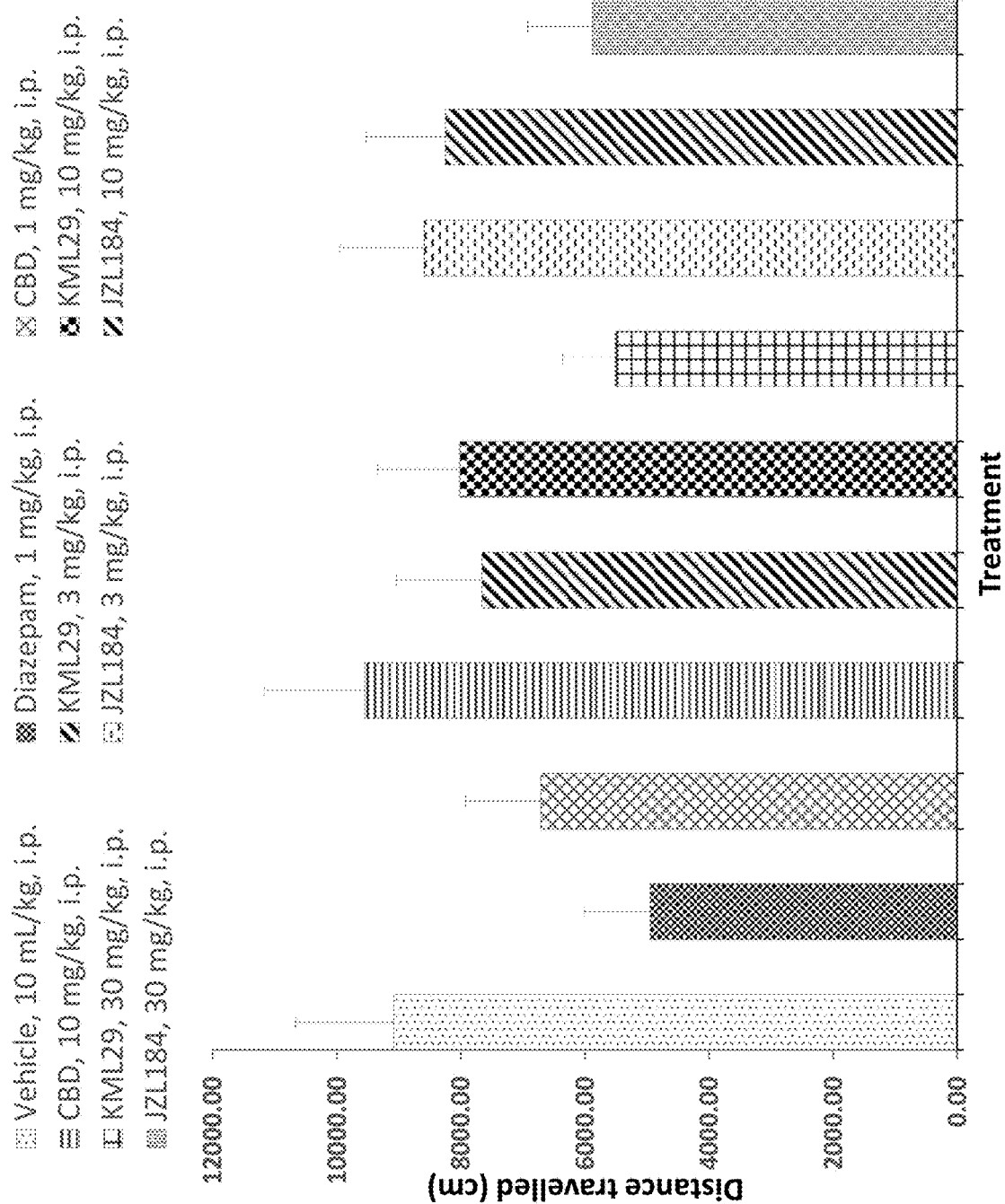
FIG. 1 shows the results of a Dose-response studies in mice. The mean ($\pm$S.E.M) effect of Cannabidiol, KML29, and JZL184 on locomotion (cumulative) are shown. (Mean$\pm$SEM of distance traveled in cm, One-way ANOVA followed by Bonferroni's multiple comparison test, *$p<0.05$, N=8).

The description is directed to a formulation for treating an affective disorder such for example a mood disorder comprising in combination an effective amount of one or more than one cannabinoid receptor agonist (CB receptor agonist) such for example cannabinoid and an effective amount of one or more than one serine hydrolase enzyme inhibitor such for example one or more than one monoacylglycerol lipase (MAGL) inhibitor.

Without wishing to be bound by theory, it is believed that the combination of one or more than one CB receptor agonist (such as for example cannabinoid that will not elicit psychoactive side effects such for example cannabidiol (CBD)) with one or more than one serine hydrolase enzyme inhibitor such as for example MAGL inhibitor (for example JZL184 or KML2) may offer an improved therapeutic outcome to subjects with an affective disorder. Particularly, in subjects with benzodiazepine or cannabis tolerance issues and/or subjects that do not want to use whole cannabis plant product or crude/standardized extracts thereof.

It is believed that because of the combination of the one or more than one CB receptor agonist with the one or more than one serine hydrolase enzyme inhibitor, the therapeutic dose required for an anxiolytic effect of a non-psychoactive CB receptor agonist (for example cannabinoids such as cannabidiol) may be lowered, when compared to formulations that comprise serine hydrolase enzyme inhibitor (such for example MAGL inhibitor), but not one or more than one CB receptor agonist and not one or more than one serine hydrolase enzyme inhibitor. Therefore, the formulation described herein may help to mitigate and avoid issues related to tolerance and dependency seen during the use of one CB receptor agonist such as cannabinoids and also can be used as a replacement for benzodiazepines such as diazepam.

It is further believed that the combination of the compounds may act synergistically, i.e. exhibits a greater than additive effect. In particular, the combination of one or more than one CB receptor agonist with one or more than one serine hydrolase enzyme inhibitor may act synergistically, i.e. exhibits a greater than additive effect.

Furthermore, it is believed that one or more than one CB receptor agonist, and one or more than one serine hydrolase enzyme inhibitor may lower doses of CB receptor agonist and serine hydrolase enzyme inhibitor may be prescribed to patients, thereby reducing the cost and increasing the profit margin of the therapeutic anxiolytic product.

The therapeutic dose of CB receptor agonist and serine hydrolase enzyme inhibitor may mitigate the deleterious side effects of benzodiazepines. Without wishing to be bound by theory, it is believed that the synergism between CB receptor agonist and serine hydrolase enzyme inhibitor, results in a lower effective dose of CB receptor agonist. Furthermore, CB receptor agonist such for example cannabidiol such as CBD has bioactivities (e.g., described anti-seizure, anti-depression effects, mitigation of effects on memory caused by THC, appetite modulating) that might mitigate the psychoactive and other deleterious side effects for example those of GABA(A) modulator drugs, such as benzodiazepines. In addition, the formulation described herein avoids the negative side effects of smoking.

By using a formulation with one or more than one CB receptor agonist in combination with one or more than one serine hydrolase enzyme inhibitor it is possible to exactly control the dose of each bioactive molecule in the formulation. In contrast, this control may not be possible when using extracts of cannabis, where the side effects of using whole cannabis products that contain psychoactive molecules may not be avoided.

CB Receptor Agonist

By the term "Cannabinoid receptor agonist" or "CB receptor agonist" it is meant a substance, composition, compound or molecule that act on one or more than one CB receptor, such for example cannabinoid receptor type 1 ($CB_1$) or cannabinoid receptor type 2 (CB2) or may otherwise interact or modulate the endocannabinoid system or other cannabinoid-binding proteins such as for example transient receptor potential cation channels (e.g., TRPV1, TRPV2, TRPA1, TRPM8), GPR (e.g., GPR55, GPR18, GPR119) receptors, serotonin receptors (e.g., 5-HT1A), endocannabinoid transporter and reuptake proteins, α3 glycine receptors, adenosine A1 receptors or α2 adrenoceptors.

Cannabinoid receptors may be activated by three major groups of ligands, endocannabinoids (produced by the mammalian body), phytocannabinoid or plant cannabinoids (produced by plants, for example, the cannabis plant) and synthetic cannabinoids (produced artificially or synthetically). The CB Receptor agonist may be a substance, composition, compound or molecule that acts on $CB_1$. In another example the CB Receptor agonist may be a substance, composition, compound or molecule that acts on $CB_2$.

The formulation as described herein may comprise an effective amount of one or more than one CB receptor agonist from about 1 mg to about 1000 mg, or any amount therebetween. For example, the effective amount of the one or more than one CB receptor agonist may be 1 mg, 2 mg, 3 mg, 4 mg, 5 mg, 10 mg, 20 mg, 30 mg, 40 mg, 50, mg, 100 mg, 200 mg, 300 mg, 400 mg, 500 mg, 600 mg, 700 mg, 800 mg, 900 mg, 1000 mg, or any amount therebetween. The one or more than one CB receptor agonist may, for example, be a cannabinoid, a cannabidiol (CBD) or a CBD derivative, or a CBD precursor, or a CBD analog.

Furthermore, an effective dose of the one or more than one CB receptor agonist may comprise from about 0.05 mg/kg to about 150 mg/kg or any amount therebetween. For example, the effective dose of the one or more than one CB receptor agonist may be 0.05 mg/kg, 0.06 mg/kg, 0.07 mg/kg, 0.08 km/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 km/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg or any amount therebetween.

Cannabinoid

In one example the CB receptor agonist may be one or more than one cannabinoid or a cannabinoid derivative or analog. For example, the cannabinoid may be a phytocannabinoid. For example, the cannabinoid may be extracted and/or purified from cannabis plants.

The term "cannabis plant(s)" encompasses wild type *Cannabis sativa* and also variants thereof, including cannabis chemovars (varieties characterized by virtue of chemical composition) which naturally contain different amounts of individual cannabinoids, also *Cannabis sativa* subspecies indica including the variants var. indica and var. kafiristanica, *Cannabis indica* and also plants which are the result of genetic crosses, self-crosses or hybrids thereof. Furthermore, cannabis plants include for example the species *Cannabis sativa*, *Cannabis indica* or *Cannabis ruderalis*. The term "cannabis plant material" is to be interpreted accordingly as encompassing plant material derived from one or more cannabis plants irrespective of varieties. For the avoidance of doubt, it is hereby stated that "cannabis plant material" includes herbal cannabis and dried cannabis biomass.

For example, cannabis plant material derived from cannabis plants having a relatively high content of CBD (as CBDA and/or CBD) may be used. For example, cannabis varieties (chemovars) having a CBDA/CBD content of >90% of the total cannabinoid content may be used. In particular, phytocannabinoid may be extracted or purified for example from high CBD strains such for example Charlotte's Web or Avidekal.

Non limiting examples of phytocannabinoid include cannabidiol (CBD) or CBD derivatives, Abnormal CBD, Cannabigerol (CBG), Cannabichromene (CBC), Cannabicyclol (CBL), Cannabivarin (also known as cannabivarol or CBV), Tetrahydrocannabivarin (THCV, THV), Cannabidivarin (CBDV), Cannabichromevarin (CBCV), Cannabigerovarin (CBGV), Cannabigerol Monomethyl Ether (CBGM). In one non-limiting example, the cannabinoid may be a cannabidiol (CBD) extracted and purified from one or more high CBD strain such for example Charlotte's Web or Avidekal.

In another example, the cannabinoid may be a synthetic cannabinoid (also known as synthetic cannabis (synthetic marijuana), or synthetic cannabinoid receptor agonists), for example, but not limited to, Cannabicyclohexanol (CP 47,497), JWH-018, JWH-073, or HU-210, Epigallocatechin, Epicatechin, Kavain, Yangonin, N-Arachidonoyl dopamine, Cannabidiol (CBD), Cannabinol (CBN), HU-210, 11-Hydroxy-Δ9-tetrahydrocannabinol (11-OH-THC), dronabinol or Levonantradol (CP 50,556-1).

The formulation as described herein may comprise an effective amount of one or more than one cannabinoid from about 1 mg to about 1000 mg, or any amount therebetween. For example, the effective amount of the one or more than one cannabinoid may be 1 mg, 2 mg, 3 mg, 4 mg, 5 mg, 10 mg, 20 mg, 30 mg, 40 mg, 50, mg, 100 mg, 200 mg, 300 mg, 400 mg, 500 mg, 600 mg, 700 mg, 800 mg, 900 mg, 1000 mg, or any amount therebetween. The one or more than one cannabinoid may, for example, be cannabidiol (CBD) or a CBD derivative, or a CBD precursor, or a CBD analog. In one example, the formulation described herein may, therefore, comprise an effective amount of CBD or a CBD derivative from about 1 mg to about 1000 mg, or any amount there between. For example, the effective amount of CBD or the CBD derivative may be 1 mg, 2 mg, 3 mg, 4 mg, 5 mg, 10 mg, 20 mg, 30 mg, 40 mg, 50, mg, 100 mg, 200 mg, 300 mg, 400 mg, 500 mg, 600 mg, 700 mg, 800 mg, 900 mg, 1000 mg, or any amount therebetween.

Furthermore, an effective dose of the one or more than one cannabinoid may comprise from about 0.05 mg/kg to about 150 mg/kg or any amount therebetween. For example, the effective dose of the one or more than one cannabinoid may be 0.05 mg/kg, 0.06 mg/kg, 0.07 mg/kg, 0.08 km/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 km/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg or any amount therebetween. The one or more than one cannabinoid may, for example, be cannabidiol (CBD) or a CBD derivative, or a CBD precursor, or a CBD analog.

Purification/Extraction

Methods of preparing cannabinoids from the plant in substantially pure form starting from plant material are known in the art. For example, WO 02/064109 which is herein incorporated by reference [8], describes a general method for obtaining whole extracts from cannabis plant material. WO 02/32420 discloses a process for preparing, for example, $\Delta^9$-THC from plant material [9]. It utilizes $CO_2$ extraction and ethanol precipitation to obtain "primary extracts" containing $\Delta^9$-THC and CBD, with reduced amounts of, for example, monoterpenes, sesquiterpenes, hydrocarbons, alkaloids, flavonoids, and chlorophylls. The CBD is then converted to $\Delta^9$-THC by a catalyzing reaction. ODCCP Bulletin on Narcotics [10] discloses a method of isolating CBD, THC, and CBN using preparative gas chromatography. Another issue of ODCCP Bulletin on Narcotics [11] describes a multi-solvent extraction process using petroleum ether and methanol. Smith and Vaughan in Journal of Pharmacy and Pharmacology [12] disclose the use of various solvents as an extraction medium for solubilizing cannabinoids. U.S. Pat. No. 7,700,368, which is herein incorporated by reference [13], describes a purification process for prepare purified forms of cannabinoid and cannabinoid acid constituents of cannabis herb, including the cannabinoid acids Δ9 THCA and CBDA, the corresponding free cannabinoids Δ9 THC and CBD, and the minor cannabinoids, by using a combination of solvent extraction, chromatography and re-crystallization steps. Furthermore, WO 2004026802, which is herein incorporated by reference [14], describes a method for preparing cannabidiol from plant material. Substantially pure cannabidiol (CBD) from plant material is obtained from cannabidiol-containing extract of the plant material by dissolving the extract in a solvent to form a solution, removing insoluble material from this solution and evaporating the solvent from the solution to obtain substantially pure cannabidiol. Furthermore, an example of the purification of cannabidiol is described in Waters Application Notes [15].

It is preferred to use cannabis plant material derived from cannabis plants having a relatively high content of CBD (as CBDA and/or CBD). For example, by using standard selective breeding techniques cannabis varieties with high CBD content may be developed that may, for example, have a CBDA/CBD content of >90% of the total cannabinoid content for example, for example, Charlotte's Web or Avidekal.

If the plant material from which CBD is to be prepared contains significant amounts of the cannabinoid acid CBDA then the plant material may be subjected to a decarboxylation step to convert CBDA to the free cannabinoid CBD. This is may be carried out prior to preparation of the CBD-containing plant extract or may form part of this extraction process.

A "substantially pure" preparation of cannabinoid such for example cannabidiol (CBD) is defined as a preparation having a chromatographic purity of 95% or greater, more preferably 96% or greater, more preferably 97% or greater, more preferably 98% or greater, more preferably 99% or greater, and most preferably 99.5% or greater as determined by area normalization of an HPLC UV profile.

Serine Hydrolase Enzyme Inhibitor

Serine hydrolases (SHs) are one of the largest and most diverse enzyme classes in mammals. They play fundamental roles in virtually all physiological processes and are targeted by drugs to treat diseases such as for example stress, anxiety, mood disorders and neurodegenerative disorders. There are ~240 human serine hydrolases, which can be divided into two near-equal-sized subgroups—the serine proteases (~125 members) and the 'metabolic' serine hydrolases (~115 members) [16]. Many serine hydrolases have emerged as enzymes with therapeutic potential and are the focus of intense inhibitor discovery programs. Compounds that act through covalent mechanisms have proved to be especially effective at selectively inhibiting serine hydrolases.

By the term "serine hydrolase enzyme inhibitor", "serine hydrolase inhibitor", "hydrolase inhibitor" or "SH inhibitor" it is meant a substance, composition, compound or molecule that inhibits, blocks, decreases or deactivates the activity of an enzyme that belongs to the serine hydrolase superfamily. The serine hydrolase enzyme may contain the classical GXSXG consensus sequence common to most serine hydrolases. The catalytic triad in the serine hydrolase enzyme may comprise a Ser122, His269, and Asp239. Non-limiting examples of serine hydrolase enzyme inhibitors are, acetylcholinesterase (ACHE) inhibitors: Rivastigmine, Donepezil, Galantamine, Tacrine; dipeptidyl peptidase-4 (DPP4) inhibitors: Sitagliptin, Saxagliptin, Linagliptin, Vildagliptin, Alogliptin; Pancreatic/Gastric lipase inhibitors: Orlistat; Thrombin inhibitors: Dabigatran, Argatroban; Factor Xa inhibitors: Rivaroxaban; Thrombosis Human neutrophil elastase inhibitors: Sivelestat; fatty acid amide hydrolase (FAAH) inhibitors: OL-135, URB597, PF-04457845; fibroblast activation protein (FAP)/dipeptidyl peptidase inhibitors: PT-100; endothelial lipase (LIPG) inhibitors: Sulfonylfuran urea 1; phospholipase A2 (PLA2G7) inhibitors: Darapladib; prolylcarboxypeptidase (PRCP) inhibitors: Compound 80; prolyl endopeptidase (PREP) inhibitors: S17092, JTP-4819; triacylglycerol Hydrolase (TGH) inhibitors: GR148672X; arylacetamide deacetylase-like 1 (AADACL1) inhibitors: AS115, JW480; alpha/beta-Hydrolase (ABHD6) inhibitors: WWL123; alpha/beta-Hydrolase (ABHD11) inhibitors: AA44-2, WWL222; acyl-peptide hydrolase (APEH) inhibitor: AA74-1; Monoacyl glycerol lipase (MAGL) inhibitors: JZL184; platelet-activating factor acetylhydrolase-2 (PAFAH2) inhibitor: AA39-2; protein methylesterase-1 (PME-1) ABL127; among others.

A non-limiting example of a of a serine hydrolase enzyme inhibitor is an inhibitor of Monoacyl glycerol lipase (MAGL). Therefore, the serine hydrolase enzyme inhibitor may be for example be one or more than one MAGL inhibitor.

The formulation as described herein may comprise an effective amount of one or more than one serine hydrolase enzyme inhibitor from about 1 mg to about 1000 mg, or any amount therebetween. For example, the effective amount of the one or more than one serine hydrolase enzyme inhibitor may be 1 mg, 2 mg, 3 mg, 4 mg, 5 mg, 10 mg, 20 mg, 30 mg, 40 mg, 50, mg, 100 mg, 200 mg, 300 mg, 400 mg, 500 mg, 600 mg, 700 mg, 800 mg, 900 mg, 1000 mg, or any amount therebetween. The one or more than one serine hydrolase enzyme inhibitor may for example, a MAGL inhibitor such for example JZL184, a JZL184 derivative, KML29 or KML29 derivative.

Furthermore, an effective dose of the one or more than one serine hydrolase enzyme inhibitor may comprise from about 1 mg/kg to about 150 mg/kg or any amount therebetween. For example, the effective dose of the one or more than one serine hydrolase enzyme inhibitor may be 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg or any amount therebetween. The one or more than one serine hydrolase enzyme inhibitor may for example be a MAGL inhibitor such for example, JZL184, a JZL184 derivative, KML29 or a KML29 derivative.

Monoacyl Glycerol Lipase (MAGL) Inhibitor

Monoacylglycerol lipase (MAGL), also known as MAG lipase, MAGL, MAGL enzyme, MGL or MGLL is an enzyme belonging to α/β-hydrolase family. They are key in the hydrolysis of endocannabinoid 2-arachidonoylglycerol (2-AG). In humans, MAGL is encoded by the MGLL gene. MAGL is a 33-kDa, membrane-associated member of the serine hydrolase superfamily and contains the classical GXSXG consensus sequence common to most serine hydrolases. MAGL is a principal degradative enzyme for 2-AG by hydrolyzing 2-AG into glycerol and arachidonic acid (AA).

By the term "monoacyl glycerol lipase (MAGL) inhibitor", "monoacyl glycerol lipase inhibitor", "MAGL inhibitor", "MAGL enzyme inhibitor", "MAGL inhibitor compound" "inhibitor of MAGL", "inhibitor of the activity of MAGL" or "MAGL antagonist" it is meant a substance, composition, compound or molecule that inhibits, blocks, decreases or inactivates the activity of the MAGL enzyme. The MAGL inhibiting substance, composition, compound or molecule may bind to any of the following elements: the gene that encodes the MAGL enzyme, transcription factors of said gene, any of the expression products of said gene, for example, without being limited thereto, the messenger RNA of the MAGL enzyme, and decreases or inhibits the expression and the activity of the molecule to which it binds, and/or its intracellular signaling, thereby leading to total or partial inhibition of the activity of the MAGL enzyme. MAGL inhibitors include compounds that interfere with the expression, modification, regulation or activation of MAGL or compounds that down-regulate one or more of the normal biological activities of MAGL (e.g., its serine hydrolase activity). In particular, one or more than one MAGL inhibitors may block or inhibit the enzymatic activities of MAGL. For example, the MAGL inhibitors may target the nucleophilic cysteine residues (Cys201, Cys208, and Cys242) located close to the catalytic site of MAGL or the MAGL inhibitor may target the nucleophilic Ser122 residue of MAGL.

As used herein, the term "inhibit", "inhibition" or "inhibiting" refers to the reduction or suppression of the activity of a serine hydrolase enzyme for example a MAGL enzyme or a significant decrease in the baseline activity of a biological activity or process of the serine hydrolase enzyme catalyzed reaction. The inhibition of serine hydrolase enzyme such for example MAGL may be irreversible or the inhibition of serine hydrolase enzyme such as for example MAGL may be reversible, therefore the one or more than one serine hydrolase enzyme inhibitor may be an irreversible serine hydrolase enzyme inhibitor or the one or more than one serine hydrolase enzyme inhibitor may be a reversible serine hydrolase enzyme inhibitor.

MAGL antagonist compounds which also inhibit other brain serine hydrolases (e.g., FAAH) may interfere with the various biological functions mediated by those other enzymes. Such nonselective inhibitors of MAGL may have unwanted side effects. Thus, molecules that selectively inhibit the MAGL enzyme are preferred in the current applications. The one or more than one MAGL inhibitor may specifically inhibit MAGL enzymatic activity while causing no significant effect on the other brain serine hydrolases (e.g., FAAH). Accordingly, the one or more than one MAGL inhibitor may be a selective MAGL inhibitor.

The one or more than one MAGL inhibitor may be selected from the list consisting of, without being limited thereto: antagonists against the MAGL enzyme (preferably chemical), silencing RNA or specific antibody against the MAGL enzyme (preferably, the antibody is monoclonal).

Examples of chemical inhibitors of the activity of the MAGL enzyme are, without being limited thereto, Maleimide-based MAGL inhibitors (N-ethylmaleimide (NEM), N-arachidonylmaleimide (NAM), 1-biphenyl-4-ylmethyl-maleimide); Natural compounds as MAGL inhibitors (pristimerin and euphol); Disulfide-based MAGL inhibitors (disulfiram and related analogues); Isothiazolinone-based MAGL inhibitors (octhilinone); Carbamate-based MAGL inhibitors (URB602 (104) and URB602 analogues, 4-bisarylcarbinol analogue JZL184, 4-aryloxybenzyl-based analogue JZL195, JZL184, JZL195, KML29, JW642, [2,4-dinitrophenyl-4-benzhydrylpiperazine-1-carbodithioate] (CK16), 2,4-dinitrophenyl-4-(4-tert-butylbenzyl)piperazine-1-carbodithioate (CK37), and MJN110); Urea-based MAGL inhibitors (AM6701, SAR629, ML30, JJKK-048, 1,2,4-triazole analogue of JZL184); miscellaneous MAGL inhibitors (OMDM169), silencing RNA and specific antibody against the MAGL enzyme.

The one or more than one MAGL inhibitor may be for example JZL184 or KML29. JZL184 (4-nitrophenyl-4-[bis(1,3-benzodioxol-5yl)(hydroxy)methyl]piperidine-1-carboxylate) is an irreversible inhibitor for MAGL. KML29 ([4-(8-Chloro-5,6-dihydro-11H-benzo[5,6]cyclohepta[1,2-b]pyridin-11-ylidene)-1-piperidinyl](1H-1,2,4-triazol- 1-yl)methanone) is a selective reversible inhibitor of MAGL.

The formulation as described herein may comprise an effective amount of one or more than one MAGL inhibitor from about 1 mg to about 1000 mg, or any amount therebetween. For example, the effective amount of the one or more than one MAGL inhibitor may be 1 mg, 2 mg, 3 mg, 4 mg, 5 mg, 10 mg, 20 mg, 30 mg, 40 mg, 50, mg, 100 mg, 200 mg, 300 mg, 400 mg, 500 mg, 600 mg, 700 mg, 800 mg, 900 mg, 1000 mg, or any amount therebetween. The one or more than one MAGL inhibitor may, for example, be JZL184 or a JZL184 derivative and KML29 or KML29 derivative.

In one example, the formulation described herein may, therefore, comprise an effective amount of JZL184 or a JZL184 derivative from about 1 mg to about 1000 mg, or any amount therebetween. For example, the effective amount of JZL184 or a JZL184 derivative may be 1 mg, 2 mg, 3 mg, 4 mg, 5 mg, 10 mg, 20 mg, 30 mg, 40 mg, 50, mg, 100 mg, 200 mg, 300 mg, 400 mg, 500 mg, 600 mg, 700 mg, 800 mg, 900 mg, 1000 mg, or any amount therebetween.

In one example, the formulation described herein may, therefore, comprise an effective amount of KML29 or a KML29 or their derivatives from about 1 mg to about 1000 mg, or any amount therebetween. For example, the effective amount of KML29 or a KML29 or their derivatives may be 1 mg, 2 mg, 3 mg, 4 mg, 5 mg, 10 mg, 20 mg, 30 mg, 40 mg, 50, mg, 100 mg, 200 mg, 300 mg, 400 mg, 500 mg, 600 mg, 700 mg, 800 mg, 900 mg, 1000 mg, or any amount therebetween.

Furthermore, an effective dose of the one or more than one MAGL inhibitor may comprise from about 1 mg/kg to about 100 mg/kg or any amount therebetween. For example, the effective dose of the one or more than one MAGL inhibitor may be 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, or any amount therebetween. The one or more than one MAGL inhibitor may, for example, be JZL184 or a JZL184 derivative and KML29 or KML29 derivative.

The term "effective amount" or "therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, etc. In one non-limiting embodiment, the term "effective amount" or "therapeutically effective amount" refers to the amount of the compound within the formulation of the present invention that, when administered to a cell, or a tissue, or a non-cellular biological material, or a medium, is effective to at least partially reducing or inhibiting the activity of MAGL, ABHD6 or ABHD 12; or at least partially reducing or inhibiting the expression of MAGL, ABHD6 or ABHD 12. In another non-limiting embodiment, the term "effective amount" or "therapeutically effective amount" refers to the amount of the compound or compounds within a formulation of the present invention that, when administered to a subject, is effective to at least partially alleviating, inhibiting, and/or ameliorating an affective disorder.

Affective Disorder

The formulation described herein may be used for treating "affective disorder". The term "affective disorder" refers to any type of mood disorder with symptoms including, but not limited to, depression, anxiety, and/or psychosis. These disorders are characterized by various symptoms including, but not limited to interference with the ability to work, study, sleep, eat, and enjoy once pleasurable activities. Additional symptoms of depression may include persistent sadness, anxiety, or "empty" mood, feelings of hopelessness, pessimism, guilt, worthlessness, or helplessness, loss of interest or pleasure in hobbies and activities that were once enjoyed, including sex, decreased energy, fatigue, and a sense of being "slowed down," restlessness, irritability, difficulty concentrating, remembering, or making decisions, sleep disturbances, such as insomnia, early-morning awakening, or oversleeping, loss of appetite and/or weight loss or overeating and weight gain, thoughts of death or suicide and/or suicide attempts, and persistent physical symptoms that do not respond to treatment, such as headaches, digestive disorders, and chronic pain.

In one example the formulation described herein may be used for treating anxiety. Non-limiting examples of anxiety may comprise anxiety disorder, phobias, panic disorder, panic attacks, obsessive-compulsive disorder, post-traumatic stress disorder (PTSD), separation anxiety disorder, situational anxiety disorder, stress or combinations thereof.

Synergy

Without wishing to be bound by theory, it is believed that when one or more than one CB receptor agonist and one or more than one serine hydrolase enzyme inhibitor are combined a synergistic effect is achieved.

Thus, one or more than one serine hydrolase enzyme inhibitor (for example a MAGL inhibitor such as JZL184 or KML29) may be administered in combination with one or more than one CB receptor agonist (for example cannabinoid) a to treat anxiety using lower doses of each agent than if the agents were administered alone or separately, thus reducing the side effects of can the CB receptor agonist, and/or serine hydrolase enzyme inhibitor when compared to the side effects that each of the agents would exhibit when administered alone. Therefore, a synergistic result may be obtained by administering one or more than one serine hydrolase enzyme inhibitor (such for example MAGL inhibitor) with one or more CB receptor agonist (such for example cannabinoid).

Furthermore, the therapeutic dose of one or more than one CB receptor agonist (such for example cannabinoid) or the one or more than one serine hydrolase enzyme inhibitor (such for example MAGL inhibitor) may be decreased thereby increasing cost efficiency/profit of the product. Furthermore, the one or more than one CB receptor agonist may mitigate side effects of a GABA(A) modulator such as benzodiazepine, as it has anti-depressive effects, anti-seizure effects, and mitigate negative effects on memory of other drugs such as THC.

By "synergistic," it is meant that the combination of two or more agents, for example, the combination of one or more than one CB receptor agonist (such for example cannabinoid) and one or more than one serine hydrolase enzyme inhibitor (such for example MAGL inhibitor) yield a combination index (CI)<1.0. CI for the drug combinations when determined with the Chou-Talalay combination index method using CompuSyn software [17, 18]. The drug combination may be considered synergism if CI<1, antagonism if CI>1, and additive effect if CI=1.

Therefore, the formulation may comprise synergistic combination of one or more than one serine hydrolase inhibitor (SHI) and one or more than one CB receptor agonist (CB). For example, the following combinations of effective dose of the one or more than one serine hydrolase inhibitor (SHI) and one or more than one CB receptor agonist (CB) may be provided:

| SHI (mg/kg) | CB (mg/kg) | | | | | | | | | | | |
| --- | --- | --- | --- | --- | --- | --- | --- | --- | --- | --- | --- | --- |
| | 0.01 | 0.02 | 0.04 | 0.05 | 0.06 | 0.07 | 0.08 | 0.09 | 0.1 | 0.2 | 0.3 | 0.4 |
| 0.01 | x | x | x | x | x | x | x | x | x | x | x | x |
| 0.02 | x | x | x | x | x | x | x | x | x | x | x | x |
| 0.03 | x | x | x | x | x | x | x | x | x | x | x | x |
| 0.04 | x | x | x | x | x | x | x | x | x | x | x | x |
| 0.05 | x | x | x | x | x | x | x | x | x | x | x | x |
| 0.06 | x | x | x | x | x | x | x | x | x | x | x | x |
| 0.07 | x | x | x | x | x | x | x | x | x | x | x | x |
| 0.08 | x | x | x | x | x | x | x | x | x | x | x | x |
| 0.09 | x | x | x | x | x | x | x | x | x | x | x | x |
| 0.1 | x | x | x | x | x | x | x | x | x | x | x | x |
| 0.2 | x | x | x | x | x | x | x | x | x | x | x | x |
| 0.3 | x | x | x | x | x | x | x | x | x | x | x | x |
| 0.4 | x | x | x | x | x | x | x | x | x | x | x | x |
| 0.5 | x | x | x | x | x | x | x | x | x | x | x | x |
| 0.6 | x | x | x | x | x | x | x | x | x | x | x | x |
| 0.7 | x | x | x | x | x | x | x | x | x | x | x | x |
| 0.8 | x | x | x | x | x | x | x | x | x | x | x | x |
| 0.9 | x | x | x | x | x | x | x | x | x | x | x | x |
| 1 | x | x | x | x | x | x | x | x | x | x | x | x |
| 2 | x | x | x | x | x | x | x | x | x | x | x | x |
| 3 | x | x | x | x | x | x | x | x | x | x | x | x |
| 4 | x | x | x | x | x | x | x | x | x | x | x | x |
| 5 | x | x | x | x | x | x | x | x | x | x | x | x |
| 6 | x | x | x | x | x | x | x | x | x | x | x | x |
| 7 | x | x | x | x | x | x | x | x | x | x | x | x |
| 8 | x | x | x | x | x | x | x | x | x | x | x | x |
| 9 | x | x | x | x | x | x | x | x | x | x | x | x |
| 10 | x | x | x | x | x | x | x | x | x | x | x | x |
| 11 | x | x | x | x | x | x | x | x | x | x | x | x |
| 12 | x | x | x | x | x | x | x | x | x | x | x | x |
| 13 | x | x | x | x | x | x | x | x | x | x | x | x |
| 14 | x | x | x | x | x | x | x | x | x | x | x | x |
| 15 | x | x | x | x | x | x | x | x | x | x | x | x |
| 16 | x | x | x | x | x | x | x | x | x | x | x | x |
| 17 | x | x | x | x | x | x | x | x | x | x | x | x |
| 18 | x | x | x | x | x | x | x | x | x | x | x | x |
| 19 | x | x | x | x | x | x | x | x | x | x | x | x |
| 20 | x | x | x | x | x | x | x | x | x | x | x | x |
| 21 | x | x | x | x | x | x | x | x | x | x | x | x |
| 22 | x | x | x | x | x | x | x | x | x | x | x | x |
| 23 | x | x | x | x | x | x | x | x | x | x | x | x |
| 24 | x | x | x | x | x | x | x | x | x | x | x | x |
| 25 | x | x | x | x | x | x | x | x | x | x | x | x |
| 26 | x | x | x | x | x | x | x | x | x | x | x | x |
| 27 | x | x | x | x | x | x | x | x | x | x | x | x |
| 28 | x | x | x | x | x | x | x | x | x | x | x | x |
| 29 | x | x | x | x | x | x | x | x | x | x | x | x |
| 30 | x | x | x | x | x | x | x | x | x | x | x | x |
| 31 | x | x | x | x | x | x | x | x | x | x | x | x |
| 32 | x | x | x | x | x | x | x | x | x | x | x | x |
| 33 | x | x | x | x | x | x | x | x | x | x | x | x |
| 34 | x | x | x | x | x | x | x | x | x | x | x | x |
| 35 | x | x | x | x | x | x | x | x | x | x | x | x |
| 40 | x | x | x | x | x | x | x | x | x | x | x | x |

-continued

| SHI (mg/kg) | CB (mg/kg) | | | | | | | | | | | | | |
|---|---|---|---|---|---|---|---|---|---|---|---|---|---|---|
| | 0.5 | 0.6 | 0.7 | 0.8 | 0.9 | 1 | 2 | 3 | 4 | 5 | 6 | 7 | 8 | 9 | 10 |
| 0.01 | x | x | x | x | x | x | x | x | x | x | x | x | x | x | x |
| 0.02 | x | x | x | x | x | x | x | x | x | x | x | x | x | x | x |
| 0.03 | x | x | x | x | x | x | x | x | x | x | x | x | x | x | x |
| 0.04 | x | x | x | x | x | x | x | x | x | x | x | x | x | x | x |
| 0.05 | x | x | x | x | x | x | x | x | x | x | x | x | x | x | x |
| 0.06 | x | x | x | x | x | x | x | x | x | x | x | x | x | x | x |
| 0.07 | x | x | x | x | x | x | x | x | x | x | x | x | x | x | x |
| 0.08 | x | x | x | x | x | x | x | x | x | x | x | x | x | x | x |
| 0.09 | x | x | x | x | x | x | x | x | x | x | x | x | x | x | x |
| 0.1 | x | x | x | x | x | x | x | x | x | x | x | x | x | x | x |
| 0.2 | x | x | x | x | x | x | x | x | x | x | x | x | x | x | x |
| 0.3 | x | x | x | x | x | x | x | x | x | x | x | x | x | x | x |
| 0.4 | x | x | x | x | x | x | x | x | x | x | x | x | x | x | x |
| 0.5 | x | x | x | x | x | x | x | x | x | x | x | x | x | x | x |
| 0.6 | x | x | x | x | x | x | x | x | x | x | x | x | x | x | x |
| 0.7 | x | x | x | x | x | x | x | x | x | x | x | x | x | x | x |
| 0.8 | x | x | x | x | x | x | x | x | x | x | x | x | x | x | x |
| 0.9 | x | x | x | x | x | x | x | x | x | x | x | x | x | x | x |
| 1 | x | x | x | x | x | x | x | x | x | x | x | x | x | x | x |
| 2 | x | x | x | x | x | x | x | x | x | x | x | x | x | x | x |
| 3 | x | x | x | x | x | x | x | x | x | x | x | x | x | x | x |
| 4 | x | x | x | x | x | x | x | x | x | x | x | x | x | x | x |
| 5 | x | x | x | x | x | x | x | x | x | x | x | x | x | x | x |
| 6 | x | x | x | x | x | x | x | x | x | x | x | x | x | x | x |
| 7 | x | x | x | x | x | x | x | x | x | x | x | x | x | x | x |
| 8 | x | x | x | x | x | x | x | x | x | x | x | x | x | x | x |
| 9 | x | x | x | x | x | x | x | x | x | x | x | x | x | x | x |
| 10 | x | x | x | x | x | x | x | x | x | x | x | x | x | x | x |
| 11 | x | x | x | x | x | x | x | x | x | x | x | x | x | x | x |
| 12 | x | x | x | x | x | x | x | x | x | x | x | x | x | x | x |
| 13 | x | x | x | x | x | x | x | x | x | x | x | x | x | x | x |
| 14 | x | x | x | x | x | x | x | x | x | x | x | x | x | x | x |
| 15 | x | x | x | x | x | x | x | x | x | x | x | x | x | x | x |
| 16 | x | x | x | x | x | x | x | x | x | x | x | x | x | x | x |
| 17 | x | x | x | x | x | x | x | x | x | x | x | x | x | x | x |
| 18 | x | x | x | x | x | x | x | x | x | x | x | x | x | x | x |
| 19 | x | x | x | x | x | x | x | x | x | x | x | x | x | x | x |
| 20 | x | x | x | x | x | x | x | x | x | x | x | x | x | x | x |
| 21 | x | x | x | x | x | x | x | x | x | x | x | x | x | x | x |
| 22 | x | x | x | x | x | x | x | x | x | x | x | x | x | x | x |
| 23 | x | x | x | x | x | x | x | x | x | x | x | x | x | x | x |
| 24 | x | x | x | x | x | x | x | x | x | x | x | x | x | x | x |
| 25 | x | x | x | x | x | x | x | x | x | x | x | x | x | x | x |
| 26 | x | x | x | x | x | x | x | x | x | x | x | x | x | x | x |
| 27 | x | x | x | x | x | x | x | x | x | x | x | x | x | x | x |
| 28 | x | x | x | x | x | x | x | x | x | x | x | x | x | x | x |
| 29 | x | x | x | x | x | x | x | x | x | x | x | x | x | x | x |
| 30 | x | x | x | x | x | x | x | x | x | x | x | x | x | x | x |
| 31 | x | x | x | x | x | x | x | x | x | x | x | x | x | x | x |
| 32 | x | x | x | x | x | x | x | x | x | x | x | x | x | x | x |
| 33 | x | x | x | x | x | x | x | x | x | x | x | x | x | x | x |
| 34 | x | x | x | x | x | x | x | x | x | x | x | x | x | x | x |
| 35 | x | x | x | x | x | x | x | x | x | x | x | x | x | x | x |
| 40 | x | x | x | x | x | x | x | x | x | x | x | x | x | x | x |

* the values for "x" are the combination of the dose of serine hydrolase inhibitor (SHI) in mg/kg in combination with the dose of CB receptor agonist (CB) in mg/kg as indicated in the table. The one or more than one serine hydrolase inhibitor (SHI) may be an MAGL inhibitor such for example, JZL184, a JZL184 derivative, KML29 or a KML29 derivative. The one or more than one CB receptor agonist (CB) may be one or more than one cannabinoid for example cannabinol (CBD).

For example the following combinations of effective dose of the one or more than one serine hydrolase inhibitor (SHI) and one or more than one CB receptor agonist (CB) may be provided: CBD (0.1 mg/kg)+KML29 (3 mg/kg), CBD (1 mg/kg)+KML29 (30 mg/kg), CBD (0.1 mg/kg)+JZL184 (3 mg/kg), and CBD (0.1 mg/kg)+JZL184 (3 mg/kg).

Pharmaceutical Compositions

In another aspect, the present disclosure relates to a pharmaceutical composition comprising the formulation described herein. The pharmaceutical composition comprising physiologically acceptable surface-active agents, carriers, diluents, excipients, smoothing agents, suspension agents, film forming substances, and coating assistants, or a combination thereof; and a compound or combination disclosed herein. Acceptable carriers or diluents for therapeutic use are well known in the pharmaceutical art and are described, for example, in Remington's Pharmaceutical Sciences, 18th Ed., Mack Publishing Co., Easton, Pa. (1990), which is incorporated herein by reference in its entirety [19]. Preservatives, stabilizers, dyes, sweeteners, fragrances, flavoring agents, and the like may be provided in the pharmaceutical composition. For example, sodium benzoate, ascorbic acid, and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound, formulation or combination of compounds disclosed herein with other chemical components, such as diluents or carriers. The pharmaceutical composition facilitates administration of the compound or formulation to an organism. Multiple techniques of administering a compound or formulation exist in the art including, but not limited to, oral, injection, aerosol, parenteral, and topical administration. Pharmaceutical compositions can also be obtained by reacting compounds or formulations with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound or formulation into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active foam of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound or formulation.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with suitable carriers or excipient(s). Techniques for formulation and administration of the compounds of the instant application may be found in "Remington's Pharmaceutical Sciences," Mack Publishing Co., Easton, Pa., 18th edition, 1990 [19].

Suitable routes of administration may, for example, include oral, rectal, transmucosal, sublingual, transdermal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds or formulation may also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tableting processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above [19].

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragée, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragée cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragée cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragée coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragée coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The formulation or pharmaceutical preparations as described herein may be used to treat anxiety in a subject. Therefore, the current disclosure also provides a method of treating anxiety by administering to a subject in need thereof with a formulation or pharmaceutical preparations as described herein.

The anxiety may comprise generalized anxiety disorder, phobias, panic disorder, panic attacks, obsessive-compulsive disorder, post-traumatic stress disorder (PTSD), separation anxiety disorder, situational anxiety disorder, stress or a combination thereof.

The treating may comprise an extended treatment period. For example, the treatment period may be at least 21 days. Furthermore, the treating period may be at least 28 days, 35 days, 42 days or any time therebetween. Furthermore, the extended treatment period may be at least 1 month, 2 months, 3 months, 4 months, 5 months, 6 months.

The treating may comprise a protracted treatment period. For example, the treatment period may be less than 21 days. For example, the treatment period may be between about 1 to about 21 days or any amount of days therebetween. For example, the treatment period may be 1 day, 2 days, 3 days, 4 day, 5 days, 6 days, 7 days, 8 days, 9 days, 10 days, 12 days, 15 days, 18 days, 21 days or any period therebetween.

The formulation may be administered to a subject orally, intradermally, intranasally, intramuscularly, intraperitoneally, intravenously, or subcutaneously. More specifically, the formulation described herewith may be administered transmucosally or orally. The transmucosal surface may be the sublingual, buccal, nasal, ocular, vaginal, and/or rectal mucosae.

The formulation may further be delivered in an appropriate aerosol, liquid, gel, or tablet/solid drug carrier with drug stabilizers/additives.

EXAMPLES

These and other objects and features of the present invention will be made apparent from the following examples. The following examples, as described, are not intended to be construed as limiting the scope of the present invention.

It will be readily understood by the skilled artisan that numerous alterations may be made to the examples and instructions given herein. For example, alterations may be made to the purification and formulation of CBD.

Extraction and Purification of Cannabidiol (CBD)

The cannabinoid (CBD) is extracted and purified from high CBD strains of cannabis by using the combination of supercritical fluid extraction and chromatography technologies known in the scientific art to a purity of greater than 95%. The CBD can also be synthesized using chemical synthesis techniques known in the scientific art.

Dried Cannabis buds were harvested from CBD rich (12.5% w/w, on dry weight basis) cannabinoid strains. The dried buds were extracted with a solvent, yielding an extract between 100-300 grams per kilogram of extract per dried buds. The resulting extract was passed through a chromatographic column(s) to fractionate CBD out of the extract. The collected CBD rich fractions (>75% CBD w/w) was further separated in a high-pressure column chromatography, to collect pure CBD (purity >99.5%).

Examples of extraction method include using 1) organic solvents (toluene and trimethyl pentane), low molecular weight chlorinated hydrocarbon (chloroform and dichloromethane), and/or low molecular weight alcohol (ethanol), or 2) a supercritical fluid (CO2) with or without an organic solvent modifier [20].

An example of the purification of cannabidiol is described in Waters Application Notes [15]. Briefly, a 500-mg portion of the extract was sonicated in 10 mL of methanol for 30 minutes and mixed using a magnetic stirrer at 300 rpm. Prior to injection, the sample was filtered through glass fiber to remove any debris. The preparative chromatographic separation was carried out using Waters Prep 150 LC System. The CBD was detected using 2489 UV/Visible detector with semi-prep TaperSlit Flow Cell. The injection volume was 320 μL. The fraction was collected using Waters Fraction Collector III. The collected fractions were pooled, and solvent was evaporated to obtain pure CBD. The method included appropriate chromatographic system (Prep 150 LC), column temperature (Ambient), flow rate (30.0 mL/min), mobile phase (mobile phase—A: water and mobile phase B—methanol), gradient (85% to 100% B over 2.5 minutes, hold at 100% B for 2 minutes), column (Sunfire C18 OBD™ Prep, 100 Å, 5 µm, 19×100 mm) and detection systems (UV at 228 nm).

Analytical chromatographic separations were carried out using the UPLC system equipped with a PDA detector. The method included the appropriate chromatographic system (Waters ACQUITY UPLC H-Class), column (ACQUITY UPLC BEH C18, 130 Å, 175 µm, 2.1×50 mm), column temperature (50° C.), flow rate (1.0 mL/min), mobile phase (mobile phase A—0.1% formic acid in water and mobile phase B—0.1% formic acid in acetonitrile), gradient (60% to 73% B over 2.5 minutes), and detection systems (UV at 228 nm).

The UPLC-determined purity of purified CBD was 99.5%.

Preclinical Studies

Dose-response Studies in Mice

The effect of CBD, KML29, and JZL184 on locomotor activity in the open field experiment was evaluated using Swiss albino mice.

A total of 88 male Swiss albino mice (~30-45 g; 7-9 weeks old) were selected and body weights were recorded. Animals were administered respective treatments (n=8) as per the group allocation repeatedly for 7 days. On the day of testing (8th day), animals were brought to the laboratory 1 h prior to acclimatize to the laboratory conditions. Mice were habituated to the arenas for a period of 30 min. Respective treatments were intraperitoneally administered (vehicle (10 mL/kg) or Diazepam (1 mg/kg) or CBD (1, 10 and 100 mg/kg) or KML29 (3, 10 and 30 mg/kg) or JZL184 (3, 10 and 30 mg/kg)) immediately post habituation. After treatment animals were placed in the open field and distance traveled by mice was tracked for 60 min. Data obtained was analyzed by Student's 't'-test or Two-way repeated measures ANOVA followed by Bonferroni's posthoc tests by using the Graph pad prism software package (Version 7.0) and a p-value below 0.05 was considered as significant.

The results indicated that diazepam at 1 mg/kg, i.p. significantly decreased the locomotion when compared with the vehicle-treated mice group. CBD at 100 mg/kg, i.p. significantly decreased the locomotion when compared with the vehicle-treated mice group. KML29 decreased the locomotion and attained significance at 30 mg/kg, i.p. when compared with vehicle-treated mice group. JZL184 decreased the locomotion in a dose-dependent manner but the effect did not reach statistical significance (FIG. 1).

Anxiolytic Effects of Formulation

The effect of CBD, KML29, and JZL184 on locomotor activity in open field was evaluated using Swiss albino mice and compared with diazepam.

A total of 48 male Swiss albino mice (~30-45 g; 7-9 weeks old) were selected and body weights were recorded. Animals were brought to the laboratory 1 h prior to acclimatize to the laboratory conditions. The open field is a black colored arena of 51×51×51 cm enclosed by black plastic walls of same dimensions. Animals were given respective intraperitoneal treatments as per the group allocation (n=8) repeatedly for 7 days. On the day of testing (8th day), mice were habituated to the arenas for a period of 30 min. Animals were given respective treatments (vehicle (10 mL/kg) or Diazepam (1 mg/kg); CBD, 0.1 mg/kg, i.p.+KML29, 3 mg/kg, i.p; CBD, 1 mg/kg, i.p.+KML29, 30 mg/kg, i.p; CBD, 0.1 mg/kg, i.p.+JZL184, 3 mg/kg, i.p; CBD, 1 mg/kg, i.p.+JZL184, 30 mg/kg, i.p) immediately post habituation. After dosing animals were placed in the open field and distance traveled by mice was tracked for 60 min using Videomot software. The experiment was carried out over a period of 3 days administered once daily (2 or 3 animals from each group experimented in a day). All formulations were freshly prepared on the day of administration/testing). Data obtained was analyzed by Student's 't'-test or Two-way repeated measures ANOVA followed by Bonferroni's posthoc tests by using the GraphPad prism software package (Version 7.02) and p-value below 0.05 was considered as significant.

Preparation of formulations: Diazepam was dissolved with sufficient volume of 5% pharmasolve and 95% of 30% w/v captisol to get the concentration of 0.10 mg/mL and was intended for intraperitoneal administration of 1 mg/kg dose at 10 mL/kg dose volume. CBD was dissolved in a calculated volume of DMSO to get the concentration of 20 mg/mL (Stock solution). The concentrations of 0.01 mg/mL and 0.10 mg/mL were prepared by diluting the stock solution with Ethanol:Alkamuls EL-620:Saline at 1:1:18 ratio. KML29 was dissolved in a calculated volume of DMSO to get the concentration of 50 mg/mL (Stock solution). The concentrations of 0.30 mg/mL and 3.00 mg/mL were prepared by diluting the stock solution with Ethanol:Alkamuls EL-620:Saline at 1:1:18 ratio. JZL184 was dissolved in a calculated volume of DMSO to get the concentration of 50 mg/mL (Stock solution). The concentrations of 0.30 mg/mL and 3.00 mg/mL were prepared by diluting the stock solution with Ethanol:Alkamuls EL-620:Saline at 1:1:18 ratio.

Figure 2:
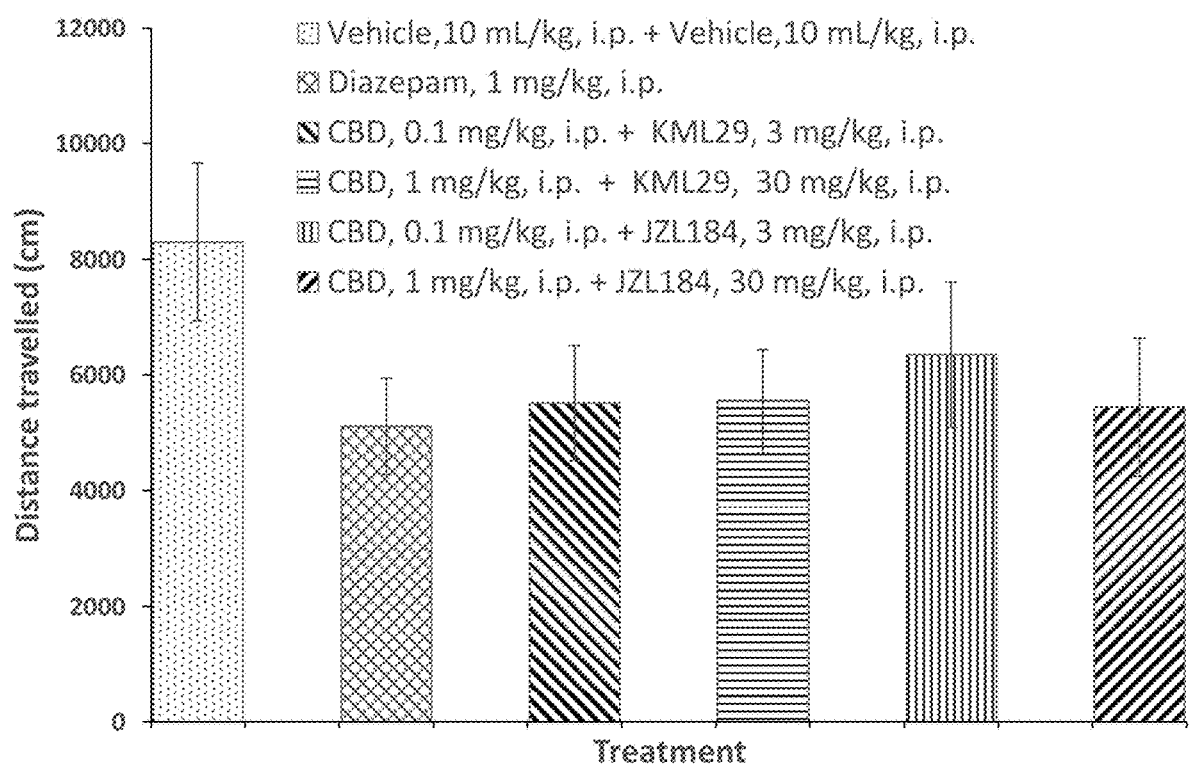
FIG. 2 shows a synergistic effect studies in mice. The mean ($\pm$S.E.M) effect of the combination of Cannabidiol and KML29, and Cannabidiol and JZL184 on locomotion (cumulative) are shown. (Mean$\pm$SEM of Distance travelled by mice in cm, \$$p<0.05$ vs. Vehicle, One-way ANOVA followed by Bonferroni's multiple comparison test, *$p<0.05$ vs. Vehicle, Student's unpaired t-test, N=7-8).

The results indicated that Diazepam at 1 mg/kg, i.p. significantly decreased the locomotion of mice when compared with vehicle treatment. KML29 at 3 and 30 mg/kg, i.p. when co-administered with CBD significantly decreased the locomotion of mice when compared with vehicle-treated group. JZL184 at 30 mg/kg, i.p. when administered in combination with CBD, 1 mg/kg, i.p. significantly decreased the locomotion of mice in a dose-dependent manner. JZL184 at 3 mg/kg, i.p. in combination with CBD, 0.1 mg/kg, i.p. comparatively decreased the locomotion, however, it did not score significance when compared to the vehicle group (FIG. 2).

Toxicity Studies—KML29 and JZL184 Formulation

Experiment 1: The objective of this study was to determine the toxicity of the combination of CBD and JZL184 following 7-day repeated intraperitoneal administration in Swiss mice. The experimental data is mentioned in Table 1-9. Forty-eight young healthy Swiss mice (6-8 weeks old; 30.92 to 34.65 g (Males) and 23.82 to 26.45 g (Females)) were divided into four groups; each comprised of 6 males and 6 females. Mice were dosed with CBD and JZL184 combination at 0.1+3 (Group II, LD), 0.5+15 (Group III, MD) and 1.0+30 mg/kg (Group IV, HD) respectively, for 7 days through intraperitoneal administration. Dose formulations were prepared daily by diluting a stock solution of CBD and JZL184 with Ethanol, Alkamuls-620 and Saline (0.9% NaCl) in the ratio of 1:1:18. Stock solutions of CBD and JZL184 were prepared at 20 mg/mL and 50 mg/mL respectively in DMSO. A concurrent vehicle control group (Group I) received vehicle on a comparable regimen at 10 mL/kg. Assessment of toxicity was based on mortality, clinical observation, and body weight, clinical and anatomic pathology. Mice were observed for mortality and clinical signs throughout the experimental period; body weights were measured daily. On the day of sacrifice, blood samples for hematology, clinical chemistry and urine were collected from all surviving mice for analysis of various parameters. Gross examination was carried out for all terminally survived mice. Tissues were collected and processed for microscopic examination.

The results indicated that CBD and JZL184 combination was well tolerated up to the highest tested dose and there was no drug-related mortality noticed in any of the treated groups (Table 1). There were no drug-related clinical signs observed throughout the experimental period up to highest tested dose. There were no drug-related adverse effects on body weight or body weight gain in mice at any dose level throughout the treatment duration (Table 2). Occasional statistically significant changes noted in females were considered incidental findings. There were no drug-related effects on hematology, clinical chemistry and urine analysis endpoints in either sex at any dose level. All statistically significant or apparent differences among hematology and clinical chemistry parameters endpoints were not considered drug related due to their negligible magnitude, sporadic nature, lack of a dose-responsive pattern, and/or relation to expected values. The tested clinical parameters (hematology, clinical chemistry and urine analysis) include WBC, RBC, HB, HCT, MCV, MCH, MCHC, Reticulocytes, Differential leukocyte count and PLT, Glucose, Total Protein, Albumin, Globulin A/G ratio, Cholesterol, Triglycerides, HDL, LDL, BUN; Sodium, Potassium and Chloride There were no drug-related effects on urinalysis parameters in either sex at any dose level (Table 3, Table 4, Table 5). There were occasional differences found in urine volume and specific gravity that were not considered toxicologically meaningful due to their sporadic nature and the inherent variability of these endpoints. The tested urine analysis parameters include Protein (mg/dL), Color, Clarity, Glucose (mg/dL), Bilirubin, Ketone (mg/dL), Specific Gravity, Blood, pH, Urobilinogen (EU/dL) and Nitrite; Leukocyte (Table 6).

There were no drug-related organ weights changes present at the terminal necropsy. Gross pathological finding included the appearance of whitish deposits in the peritoneal cavity of MD and HD animals of either sex. There were no drug-related microscopic findings present in any of the observed organs at any dose in either sex. In some of the animals of HD group, minimal peritonitis was noted which might be a local effect of the drug on the peritoneum. All other microscopic findings were considered spontaneous/incidental due to the lack of dose dependence and recognition of similar findings as background findings in the test species (Table 7).

The results showed that 7 consecutive days of intraperitoneal administration of CBD and JZL184 combinations in mice at 0.1+3, 0.5+15 and 1.0+30 mg/kg/day levels, CBD and JZL184 combination was well tolerated up to 1.0 mg/kg CBD+30 mg/kg JZL184, and No Observed Effect Level (NOEL) can be considered as 0.1 mg/kg CBD+3.0 mg/kg JZL184, and No Observed Adverse Effect Level (NOAEL) can be considered as 0.5 mg/kg CBD+15 mg/kg JZL184 (Table 8, Table 9).

Experiment 2: The objective of this study was to determine the toxicity of the combination of CBD and KML29 following 7-day repeated intraperitoneal administration in Swiss mice. The experimental data is mentioned in Tables 10-21. Forty-eight young healthy Swiss mice (6-8 weeks old; 31.07 to 34.92 g (Males) and 23.31 to 28.07 g (Females)) were divided into four groups; each comprised of 6 males and 6 females. Mice were dosed with CBD and KML29 combination at 0.1+3 (Group II, LD), 0.5+15 (Group III, MD) and 1.0+30 mg/kg (Group IV, HD) respectively, for 7 days through intraperitoneal administration. Dose formulations were prepared daily by diluting a stock solution of CBD and KML29 with Ethanol, Alkamuls-620 and Saline (0.9% NaCl) in the ratio of 1:1:18. Stock solutions of CBD and KML29 were prepared at 20 mg/mL and 50 mg/mL respectively in DMSO. A concurrent vehicle control group (Group I) received vehicle on a comparable regimen at 10 mL/kg. Assessment of toxicity was based on mortality, clinical observation, and body weight, clinical and anatomic pathology. Mice were observed for mortality and clinical signs throughout the experimental period; body weights were measured daily. On the day of sacrifice, blood samples for hematology, clinical chemistry and urine were collected from all surviving mice for analysis of various parameters. Gross examination was carried out for all terminally survived mice. Tissues were collected and processed for microscopic examination.

The results indicated that CBD and KML29 combination was well tolerated up to highest tested dose. No drug-related mortality or clinical signs were noticed at any dose level (Table 10). No drug-related changes in mean body weights and mean body weight gains were noticed throughout the treatment duration. A slight increase in WBC (mainly due to neutrophils) in mid and high dose groups was observed. No drug-related changes were noticed in clinical chemistry and urine. The tested clinical parameters include WBC, RBC, HB, HCT, MCV, MCH, MCHC, Reticulocytes, Differential leukocyte count and PLT, Glucose, Total Protein, Albumin, Globulin A/G ratio, Cholesterol, Triglycerides, HDL, LDL, BUN; Sodium, Potassium and Chloride (Tables 13, 14, 15, 16, 17). Statistically significant changes in globulin (decreased by 20-28%) in males (Table 15) and ALP (increased by 20-42%) in females (Table 16) was noticed in all drug-treated groups and considered unrelated to the drug due to either lack of dose dependency or present only in one sex. No treatment-related changes were observed when urine was analyzed for the following parameters: Protein (mg/dL), Color, Clarity, Glucose (mg/dL), Bilirubin, Ketone (mg/dL), Specific Gravity, Blood, pH, Urobilinogen (EU/dL) and Nitrite; Leukocyte. A significant increase in relative organ weights of the spleen in mid-dose (MD) females (50%) and high dose (HD) males (42%) were noticed (Table 18). Except for whitish deposits on spleen in HD animals there was no drug-related gross pathological findings were observed at any dose. Microscopically, serosal inflammation (peritonitis) was observed in visceral peritoneum of liver, kidneys, and spleen, in both sexes of mid and high dose animals. This may be due to local reaction to the peritoneal membrane where the test item comes in direct contact.

The results showed that 7 consecutive days of intraperitoneal administration of CBD and KML29 combinations in mice at 0.1+3, 0.5+15 and 1.0+30 mg/kg/day levels, CBD and KML29 combination was well tolerated up to 1.0 mg/kg CBD+30 mg/kg KML29 and No Observed Effect Level NOEL can be considered as 0.1 mg/kg CBD+3.0 mg/kg KML29.

TABLE 1

Mortality Data for formulation combination of CBD and JZL184

| Group/Dose (mg/kg) | Number of Death/Total Number of mice | |
|---|---|---|
| | Male | Female |
| I/Vehicle | 0/6 | 0/6 |
| II/0.1 mg CBD + 3 mg JZL184 | 0/6 | 0/6 |
| III/0.5 mg CBD + 15 mg JZL184 | 0/6 | 0/6 |
| IV/1 mg CBD + 30 mg JZL184 | 0/6 | 0/6 |

TABLE 2

Group Mean of Body Weight of mice (n = 6) treated with a formulation combination of CBD and JZL184

| Group/Dose (mg/kg) | Sex | Day & Body Weight (g)* | | | | | | | |
|---|---|---|---|---|---|---|---|---|---|
| | | −5 | 1 | 2 | 3 | 4 | 5 | 6 | 7 |
| I/Vehicle | Male | 29.97 ± 0.52 | 33.15 ± 1.38 | 33.91 ± 1.47 | 34.21 ± 2.01 | 34.12 ± 1.79 | 34.41 ± 1.62 | 34.96 ± 1.11 | 34.45 ± 1.48 |
| | Female | 24.23 ± 0.68 | 25.14 ± 0.99 | 24.59 ± 1.32 | 24.99 ± 1.32 | 25.03 ± 1.37 | 24.72 ± 0.72 | 25.16 ± 1.07 | 24.94 ± 0.78 |
| II/0.1 mg CBD + 3 mg ZL184 | Male | 29.97 ± 0.49 | 32.74 ± 0.92 | 33.25 ± 1.00 | 33.30 ± 1.13 | 33.58 ± 1.45 | 34.19 ± 1.23 | 34.34 ± 1.40 | 34.05 ± 1.30 |
| | Female | 24.18 ± 0.64 | 24.88 ± 0.64 | 24.65 ± 0.91 | 24.33 ± 1.04 | 24.76 ± 1.16 | 24.94 ± 0.79 | 25.46 ± 0.64 | 25.43 ± 0.96 |
| III/0.5 mg CBD + 15 mg JZL184 | Male | 29.99 ± 0.33 | 33.26 ± 0.51 | 34.32 ± 0.66 | 34.41 ± 0.60 | 35.38 ± 0.90 | 35.57 ± 0.91 | 35.76 ± 1.14 | 35.29 ± 1.03 |
| | Female | 24.20 ± 0.57 | 25.39 ± 0.19 | 25.97 ± 0.64 | 25.82 ± 0.72 | 26.35 ± 0.75 | 26.30 ± 0.73 | 26.27 ± 0.67 | 26.13 ± 0.99 |
| IV/1.0 mg CBD + 30 mg JZL184 | Male | 29.99 ± 0.32 | 32.59 ± 1.02 | 33.88 ± 0.85 | 33.78 ± 1.10 | 34.59 ± 1.36 | 34.54 ± 1.48 | 34.31 ± 1.60 | 34.27 ± 1.45 |
| | Female | 24.24 ± 0.59 | 25.58 ± 0.73 | 26.43 ± 0.78 | 26.27 ± 0.87 | 26.66 ± 0.98 | 26.42 ± 0.85 | 26.14 ± 0.69 | 26.79 ± 0.61 |

Keys: −/+ ($p < 0.05$)
*Mean ± S.D.

TABLE 3

Group Mean of Hematology Parameters in mice (n = 3) treated with a formulation combination of CBD and JZL184

| Group/Dose (mg/kg) | Sex | Hematology Parameters* | | | | |
|---|---|---|---|---|---|---|
| | | WBC ×$10^3$ cells/μL | RBC ×$10^6$ cells/μL | HB g/dL | HCT % | MCV fL |
| I/Vehicle | Male | 1.70 ± 0.91 | 8.71 ± 0.58 | 13.73 ± 0.68 | 44.27 ± 2.48 | 50.83 ± 0.47 |
| | Female | 1.81 ± 0.70 | 9.56 ± 0.48 | 15.70 ± 0.46 | 48.73 ± 1.62 | 51.00 ± 0.98 |
| II/0.1 mg CBD + 3 mg JZL184 | Male | 2.57 ± 2.70 | 8.92 ± 0.13 | 14.13 ± 0.12 | 44.33 ± 0.60 | 49.73 ± 0.81 |
| | Female | 1.53 ± 0.87 | 8.87 ± 0.21 | 14.60 ± 0.30 | 45.00 ± 0.72 | 50.73 ± 1.50 |
| III/0.5 mg CBD + 15 mg JZL184 | Male | 1.84 ± 0.61 | 9.30 ± 0.22 | 14.90 ± 0.40 | 47.13 ± 0.93 | 50.67 ± 0.21 |
| | Female | 1.92 ± 0.57 | 9.62 ± 0.09 | 15.27 ± 0.31 | 47.73 ± 0.76 | 49.60 ± 0.40 |
| IV/1 mg CBD + 30 mg JZL184 | Male | 1.61 ± 0.32 | 9.14 ± 0.26 | 14.37 ± 0.90 | 46.50 ± 2.26 | 50.83 ± 1.10 |
| | Female | 2.47 ± 0.49 | 9.42 ± 0.15 | 14.33 ± 1.78 | 47.97 ± 0.38 | 50.97 ± 1.27 |

| Group/Dose (mg/kg) | Hematology Parameters* | | | |
|---|---|---|---|---|
| | MCH pg | MCHC g/dL | Reticulocytes ×$10^9$ cells/L | PLT ×$10^3$ cells/μL |
| I/Vehicle | 15.80 ± 0.44 | 31.10 ± 0.70 | 248.37 ± 56.27 | 1472.67 ± 55.19 |
| | 16.40 ± 0.53 | 32.20 ± 0.44 | 218.93 ± 40.02 | 1009.00 ± 13.89 |
| II/0.1 mg CBD + 3 mg JZL184 | 15.87 ± 0.15 | 31.87 ± 0.23 | 236.67 ± 27.11 | 1296.33 ± 100.76 |
| | 16.50 ± 0.70 | 32.47 ± 0.50 | 247.30 ± 19.15 | 1052.00 ± 140.07 |
| III/0.5 mg CBD + 15 mg JZL184 | 16.00 ± 0.10 | 31.63 ± 0.23 | 174.53 ± 27.04 | 1185.00 ± 138.39 |
| | 15.87 ± 0.15 | 31.97 ± 0.15 | 263.37 ± 38.02 | 881.67 ± 103.74 |

TABLE 3-continued

Group Mean of Hematology Parameters in mice (n = 3) treated with a formulation combination of CBD and JZL184

| | | | | | |
|---|---|---|---|---|---|
| IV/1 mg CBD + 30 mg JZL184 | 15.73 ± 0.55 | 30.90 ± 0.52 | 179.20 ± 34.99 | 1233.67 ± 235.56 |
| | 15.20 ± 1.66 | 29.90 ± 3.91 | 179.77 ± 43.07 | 1049.00 ± 135.90 |

Keys: −/+ ($p < 0.05$)
*Mean ± S.D.

TABLE 4

Group Mean of Differential Leukocytes Count in mice (n = 3) with a formulation combination of CBD and JZL184

| Group/Dose (mg/kg) | Sex | Differential Leukocytes Count ($10^3$ cells/μL)* | | | | |
|---|---|---|---|---|---|---|
| | | Neutrophils | Lymphocytes | Monocytes | Eosinophils | Basophils |
| I/Vehicle | Male | 0.29 ± 0.25 | 1.29 ± 0.63 | 0.02 ± 0.01 | 0.09 ± 0.01 | 0.00 ± 0.01 |
| | Female | 0.20 ± 0.06 | 1.51 ± 0.67 | 0.01 ± 0.01 | 0.07 ± 0.03 | 0.01 ± 0.01 |
| II/0.1 mg CBD + 3 mg JZL184 | Male | 1.13 ± 1.67 | 1.25 ± 0.87 | 0.08 ± 0.11 | 0.09 ± 0.04 | 0.01 ± 0.01 |
| | Female | 0.27 ± 0.17 | 1.11 ± 0.81 | 0.01 ± 0.00 | 0.13 ± 0.08 | 0.00 ± 0.01 |
| III/0.5 mg CBD + 15 mg JZL184 | Male | 0.26 ± 0.12 | 1.49 ± 0.51 | 0.02 ± 0.01 | 0.07 ± 0.03 | 0.00 ± 0.01 |
| | Female | 0.32 ± 0.04 | 1.50 ± 0.51 | 0.01 ± 0.01 | 0.07 ± 0.02 | 0.01 ± 0.01 |
| IV/1 mg CBD + 30 mg JZL184 | Male | 0.27 ± 0.15 | 1.16 ± 0.09 | 0.02 ± 0.01 | 0.15 ± 0.12 | 0.00 ± 0.00 |
| | Female | 0.36 ± 0.03 | 2.00 ± 0.50 | 0.01 ± 0.01 | 0.07 ± 0.03 | 0.01 ± 0.00 |

*Mean ± S.D.

TABLE 5

Group Mean of Clinical Chemistry Parameter in mice (n = 3) treated with a formulation combination of CBD and JZL184

| Group/Dose (mg/kg) | Sex | Clinical Chemistry Parameters* | | | | |
|---|---|---|---|---|---|---|
| | | Glucose mg/dL | Total Protein g/dL | Albumin g/dL | Globulin g/dL | A/G ratio |
| I/Vehicle | Male | 176.00 ± 37.24 | 5.30 ± 0.26 | 3.00 ± 0.17 | 2.30 ± 0.10 | 1.30 ± 0.04 |
| | Female | 128.67 ± 43.75 | 5.47 ± 0.21 | 3.17 ± 0.15 | 2.30 ± 0.10 | 1.38 ± 0.08 |
| II/0.1 mg CBD + 3 mg JZL184 | Male | 170.00 ± 68.56 | 5.33 ± 0.23 | 3.00 ± 0.20 | 2.33 ± 0.12 | 1.29 ± 0.10 |
| | Female | 138.00 ± 42.14 | 5.40 ± 0.10 | 3.10 ± 0.20 | 2.30 ± 0.17 | 1.36 ± 0.19 |
| III/0.5 mg CBD + 15 mg JZL184 | Male | 211.67 ± 5.86 | 5.37 ± 0.06 | 3.03 ± 0.06 | 2.33 ± 0.06 | 1.30 ± 0.05 |
| | Female | 135.33 ± 18.45 | 5.57 ± 0.12 | 3.13 ± 0.06 | 2.43 ± 0.15 | 1.29 ± 0.10 |
| IV/1 mg CBD + 30 mg JZL184 | Male | 217.67 ± 28.01 | 5.30 ± 0.30 | 2.90 ± 0.10 | 2.40 ± 0.20 | 1.21 ± 0.06 |
| | Female | 157.33 ± 44.28 | 5.83 ± 0.31 | 3.10 ± 0.10 | 2.73 ± 0.40 | 1.16 ± 0.21 |

| Group/Dose (mg/kg) | Clinical Chemistry Parameters* | | | | |
|---|---|---|---|---|---|
| | Cholesterol mg/dL | Triglycerides mg/dL | HDL mg/dL | LDL mg/dL | BUN mg/dL |
| I/Vehicle | 142.33 ± 23.18 | 112.33 ± 45.54 | 62.23 ± 6.33 | 6.40 ± 1.59 | 17.45 ± 2.97 |
| | 107.33 ± 20.60 | 110.33 ± 18.77 | 44.57 ± 8.47 | 7.37 ± 0.29 | 15.42 ± 2.47 |
| II/0.1 mg CBD + 3 mg JZL184 | 171.67 ± 36.12 | 126.00 ± 21.66 | 74.67 ± 13.25 | 8.73 ± 1.63 | 14.64 ± 3.28 |
| | 112.67 ± 39.00 | 120.33 ± 33.50 | 45.67 ± 16.35 | 7.50 ± 1.28 | 14.80 ± 0.97 |
| III/0.5 mg CBD + 15 mg JZL184 | 171.67 ± 24.11 | 80.00 ± 24.88 | 75.23 ± 6.85 | 8.80 ± 4.25 | 15.27 ± 3.11 |
| | 124.33 ± 31.79 | 86.67 ± 22.50 | 48.93 ± 6.98 | 8.57 ± 2.97 | 16.51 ± 2.66 |
| IV/1 mg CBD + 30 mg JZL184 | 170.33 ± 41.31 | 90.33 ± 19.04 | 79.17 ± 11.93 | 9.03 ± 2.40 | 14.33 ± 0.54 |
| | 135.33 ± 47.38 | 87.33 ± 25.11 | 18.80 ± 30.23 | 12.87 ± 10.00 | 16.04 ± 2.30 |

TABLE 5-continued

Group Mean of Clinical Chemistry Parameter in mice (n = 3) treated with a formulation combination of CBD and JZL184

| Group/Dose (mg/kg) | Sex | Creatinine mg/dL | ALT U/L | AST U/L | ALP U/L | Creatine kinase U/L |
|---|---|---|---|---|---|---|
| I/Vehicle | Male | 0.39 ± 0.10 | 100.67 ± 73.00 | 91.67 ± 32.25 | 138.67 ± 35.56 | 758.00 ± 501.46 |
|  | Female | 0.40 ± 0.10 | 48.33 ± 36.12 | 121.33 ± 32.52 | 141.00 ± 50.59 | 571.67 ± 337.20 |
| II/0.1 mg CBD + 3 mg JZL184 | Male | 0.41 ± 0.14 | 69.67 ± 48.99 | 137.67 ± 51.29 | 163.67 ± 36.83 | 1066.00 ± 900.22 |
|  | Female | 0.34 ± 0.02 | 88.67 ± 65.84 | 199.67 ± 123.87 | 165.67 ± 14.05 | 932.33 ± 483.35 |
| III/0.5 mg CBD + 15 mg JZL184 | Male | 0.56 ± 0.07 | 232.00 ± 234.78 | 131.67 ± 109.66 | 139.67 ± 4.93 | 273.33 ± 14.15 |
|  | Female | 0.44 ± 0.09 | 38.67 ± 17.47 | 116.00 ± 47.32 | 155.33 ± 20.74 | 502.67 ± 169.52 |
| IV/1 mg CBD + 30 mg JZL184 | Male | 0.55 ± 0.06 | 89.00 ± 20.95 | 132.67 ± 82.66 | 131.33 ± 12.10 | 716.33 ± 868.54 |
|  | Female | 0.49 ± 0.13 | 85.00 ± 23.90 | 303.00 ± 183.52 | 86.67 ± 44.19 | 870.00 ± 323.25 |

| Group/Dose (mg/kg) | Calcium mg/dL | Magnesium mg/dL | Phosphorous mg/dL | GGT U/L | Total Bilirubin mg/dL |
|---|---|---|---|---|---|
| I/Vehicle | 9.39 ± 0.07 | 2.03 ± 0.16 | 12.12 ± 2.79 | — | 0.13 ± 0.02 |
|  | 9.40 ± 0.13 | 1.92 ± 0.06 | 11.83 ± 0.44 | — | 0.14 ± N/A*** |
| II/0.1 mg CBD + 3 mg JZL184 | 9.51 ± 0.26 | 2.08 ± 0.26 | 12.07 ± 0.73 | — | 0.15 ± 0.07 |
|  | 9.33 ± 0.31 | 2.08 ± 0.28 | 11.19 ± 1.45 | — | 0.12 ± 0.02*** |
| III/0.5 mg CBD + 15 mg JZL184 | 9.35 ± 0.32 | 2.00 ± 0.27 | 10.39 ± 1.06 | — | 0.17 ± 0.08*** |
|  | 9.40 ± 0.37 | 1.94 ± 0.15 | 11.24 ± 1.99 | — | 0.11 ± N/A** |
| IV/1 mg CBD + 30 mg JZL184 | 9.35 ± 0.26 | 2.00 ± 0.40 | 10.95 ± 1.70 | — | 0.12 ± N/A** |
|  | 9.51 ± 0.17 | 2.73 ± 0.53 | 11.32 ± 1.08 | — | — |

| Group/Dose (mg/kg) | Sex | Sodium mmol/L | Potassium mmol/L | Chloride mmol/L |
|---|---|---|---|---|
| I/Vehicle | Male | 154.34 ± 2.31 | 4.92 ± 0.52 | 110.74 ± 3.77 |
|  | Female | 153.84 ± 3.50 | 5.42 ± 0.69 | 110.12 ± 2.60 |
| II/0.1 mg CBD + 3 mg JZL184 | Male | 154.86 ± 4.04 | 5.29 ± 0.46 | 112.28 ± 5.09 |
|  | Female | 153.83 ± 0.44 | 4.97 ± 0.48 | 112.53 ± 2.11 |
| III/0.5 mg CBD + 15 mg JZL184 | Male | 151.82 ± 0.75 | 4.62 ± 0.19 | 110.11 ± 1.37 |
|  | Female | 149.61 ± 1.95 | 5.03 ± 0.47 | 111.62 ± 1.88 |
| IV/1 mg CBD + 30 mg JZL184 | Male | 150.34 ± 1.95 | 5.23 ± 0.35 | 110.43 ± 3.25 |
|  | Female | 150.85 ± 3.35 | 5.47 ± 0.82 | 110.74 ± 3.39 |

Keys: +/− (p < 0.05) indicates significantly higher/lower than control group; A (—) indicates the values were below the lower limit of quantification.
*Mean ± S.D.
**n = 1
***n = 2

TABLE 6

Summary of Urinalysis in mice treated with a formulation combination of CBD and JZL184

| Parameter | Group Dose (mg/kg) | I/Vehicle Male | I/Vehicle Female | II/0.1 gm CBD + 3 mg JZL184 Male | II/0.1 gm CBD + 3 mg JZL184 Female |
|---|---|---|---|---|---|
| Volume (mL) | Mean ± S.D. | 253.33 ± 133.67 | 225.00 ± 95.74 | 450.00 ± 57.74 | 330.00 ± 130.38 |
| Protein (mg/dL) | Negative | — | 1/4 | — | — |
|  | Trace | — | — | 2/4 | 1/5 |
|  | 30 | 3/6 | 3/4 | — | 3/5 |
|  | 100 | 3/6 | — | 2/4 | — |
|  | >300 | — | — | — | 1/5 |

TABLE 6-continued

Summary of Urinalysis in mice treated with a formulation combination of CBD and JZL184

| Parameter | | I Male | I Female | II Male | II Female |
|---|---|---|---|---|---|
| Color | Yellow | — | 4/4 | — | 5/5 |
| | Pale Yellow | 6/6 | 4/4 | 4/4 | 5/5 |
| Clarity | Clear | 6/6 | 4/4 | 4/4 | 5/5 |
| Glucose (mg/dL) | Negative | 6/6 | 4/4 | 4/4 | 5/5 |
| | 100 | — | — | — | — |
| Bilirubin | Negative | 6/6 | 3/4 | 4/4 | 5/5 |
| | Small | — | 1/4 | — | — |
| Ketone (mg/dL) | Negative | — | 1/4 | 1/4 | — |
| | Trace | — | 1/4 | 1/4 | 2/5 |
| | 15 | 5/6 | 2/4 | 2/4 | 3/5 |
| | 40 | 1/6 | — | — | — |
| Specific Gravity | Mean ± S.D. | 1.019 ± 0.004 | 1.018 ± 0.003 | 1.014 ± 0.002 | 1.020 ± 0.000 |

| | | III<br>III/0.5 mg CBD + 15 mg JZL184 | | IV<br>IV/1 mg CBD + 30 mg JZL184 | |
|---|---|---|---|---|---|
| Parameter | | Male | Female | Male | Female |
| Volume (mL) | | 243.33 ± 154.49 | 252.00 ± 108.49 | 180.00 ± 40.00 | 65.00 ± 196.15 |
| Protein (mg/dL) | | — | — | — | 2/4 |
| | | 2/6 | 1/5 | — | — |
| | | 1/6 | 3/5 | 3/4 | 1/4 |
| | | 3/6 | 1/5 | 1/4 | 1/4 |
| | | — | — | — | — |
| Color | | — | 5/5 | — | 4/4 |
| | | 6/6 | 5/5 | 4/4 | 4/4 |
| Clarity | | 6/6 | 5/5 | 4/4 | 4/4 |
| Glucose (mg/dL) | | 6/6 | 4/5 | 4/4 | 4/4 |
| | | — | 1/5 | — | — |
| Bilirubin | | 6/6 | 5/5 | 4/4 | 4/4 |
| | | — | — | — | — |
| Ketone (mg/dL) | | 1/6 | — | — | 1/4 |
| | | 2/6 | 1/5 | — | 1/4 |
| | | 3/6 | 4/5 | 4/4 | 2/4 |
| | | — | — | — | — |
| Specific Gravity | | 1.018 ± 0.003 | 1.022 ± 0.003 | 1.023 ± 0.003 | 1.024 ± 0.002 |

| | Group<br>Dose | I<br>I/Vehicle | | II<br>II/0.1 mg CBD + 3 mg JZL184 | | III<br>III/0.5 mg CBD + 15 mg JZL184 | | IV<br>IV/1 mg CBD +30 mg JZL184 | |
|---|---|---|---|---|---|---|---|---|---|
| Parameter | (mg/kg) | Male | Female | Male | Female | Male | Female | Male | Female |
| Blood | Negative | 6/6 | 3/4 | 4/4 | 4/5 | 5/6 | 4/5 | 4/4 | 4/4 |
| | Moderate | — | 1/4 | — | — | — | — | — | — |
| | Small | — | — | — | — | — | 1/5 | — | — |
| | Trace lysed | — | — | — | 1/5 | — | — | — | — |
| | Trace intact | — | — | — | — | 1/6 | — | — | — |
| pH | Mean ± S.D. | 7.50 ± 0.63 | 8.25 ± 0.50 | 7.00 ± 0.41 | 6.90 ± 0.96 | 7.42 ± 0.58 | 7.10 ± 0.42 | 7.63 ± 0.75 | 7.13 ± 0.95 |
| Urobilinogen (EU/dL) | 0.20 | 6/6 | 3/4 | 4/4 | 5/5 | 6/6 | 5/5 | 4/4 | 4/4 |
| | 1.00 | — | 1/4 | — | — | — | — | — | — |
| Nitrite | Negative | 6/6 | 4/4 | 4/4 | 5/5 | 6/6 | 5/5 | 4/4 | 4/4 |
| Leukocyte | Negative | 5/6 | 3/4 | 2/4 | 4/5 | 5/6 | 5/5 | 3/4 | 4/4 |
| | Trace | 1/6 | 1/4 | 2/4 | 1/5 | 1/6 | — | 1/4 | — |

Keys: A dash (—) indicates the absence of finding in the group, Value indicates the number of incidences except for urine volume, protein, specific gravity, and pH.

TABLE 7

Group Mean of Relative Organ Weight in mice (n = 6) treated with a formulation combination of CBD and JZL184

| Group/Dose (mg/kg) | Sex | Mean Body Weight | Relative Organ Weight (%)* | | | | | |
|---|---|---|---|---|---|---|---|---|
| | | | Liver | Kidneys | Heart | Brain | Spleen | Lung |
| I/Vehicle | Male | 32.50 ± 1.39 | 5.7207 ± 0.61 | 1.6431 ± 0.18 | 0.5821 ± 0.05 | 1.6067 ± 0.10 | 0.3568 ± 0.12 | 0.6976 ± 0.09 |
| | Female | 23.69 ± 0.95 | 5.6134 ± 0.65 | 1.3631 ± 0.09 | 0.5612 ± 0.05 | 2.0985 ± 0.10 | 0.4099 ± 0.10 | 0.7311 ± 0.05 |
| II/0.1 mg CBD + 3 mg JZL184 | Male | 31.87 ± 1.53 | 5.6234 ± 0.31 | 1.5678 ± 0.19 | 0.5436 ± 0.05 | 1.6351 ± 0.05 | 0.2879 ± 0.04 | 0.6186 ± 0.04 |
| | Female | 23.79 ± 1.15 | 5.4893 ± 0.35 | 1.4148 ± 0.09 | 0.5694 ± 0.03 | 2.1518 ± 0.12 | 0.4647 ± 0.08 | 0.7529 ± 0.06 |
| III/0.5 mg CBD + 15 mg JZL184 | Male | 33.12 ± 0.54 | 5.9895 ± 0.77 | 1.5857 ± 0.12 | 0.5389 ± 0.04 | 1.5728 ± 0.07 | 0.2826 ± 0.05 | 0.5827 ± 0.11 |
| | Female | 24.46 ± 0.62 | 5.5166 ± 0.31 | 1.3326 ± 0.12 | 0.5240 ± 0.03 | 2.0814 ± 0.10 | 0.3846 ± 0.06 | 0.7026 ± 0.05 |
| IV/1 mg CBD + 30 mg JZL184 | Male | 31.95 ± 1.18 | 5.9032 ± 0.37 | 1.4635 ± 0.10 | 0.5327 ± 0.03 | 1.5705 ± 0.06 | 0.2703 ± 0.03 | 0.6070 ± 0.05 |
| | Female | 24.59 ± 0.76 | 5.7409 ± 0.39 | 1.3056 ± 0.10 | 0.5498 ± 0.04 | 2.0427 ± 0.13 | 0.3916 ± 0.08 | 0.7497 ± 0.07 |

*Mean ± S.D.

TABLE 8

Summary of Gross Pathological Findings in mice treated with a formulation combination of CBD and JZL184

| Group | I | II | III | IV |
|---|---|---|---|---|
| Dose (mg/kg) | I/Vehicle | II/0.1 mg CBD + 3 mg JZL184 | III/0.5 mg CBD + 15 mg JZL184 | IV/1 mg CBD + 30 mg JZL184 |
| Mode of Sacrifice | TS | TS | TS | TS |
| Necropsy findings | \multicolumn{4}{c}{Incidence (No. of animals with findings/No. of animals examined)} | | | |
| | \multicolumn{4}{c}{Sex: Male} | | | |
| NAD | 6/6 | 6/6 | 5/6 | 1/6 |
| Peritoneal Cavity Whitish Deposits (1) | — | — | 1/6 | 5/6 |
| | \multicolumn{4}{c}{Sex: Female} | | | |
| NAD | 6/6 | 6/6 | 4/6 | 2/6 |
| Peritoneal Cavity Whitish Deposits (1) | — | — | 2/6 | 4/6 |

Keys: NAD—No Abnormality Detected, TS—Terminal Sacrifice, A dash (—) indicates the absence of findings, 1—Minimal.

TABLE 9

Summary of Histopathology Finding in mice treated with a formulation combination of CBD and JZL184

| | | Group | | | | | | | |
|---|---|---|---|---|---|---|---|---|---|
| | | I | | II | | III | | IV | |
| | | Dose (mg/kg) | | | | | | | |
| | | 0 mg/kg (Vehicle) | | 0.1 mg/kg CBD + 3 mg/kg JZL184 | | 0.5 mg/kg CBD + 15 mg/kg JZL184 | | 1.0 mg/kg CBD + 30 mg/kg JZL184 | |
| Sex | Severity | M | F | M | F | M | F | M | F |
| Number of animals examined | | 6 | 6 | 6 | 6 | 6 | 6 | 6 | 6 |
| Histopathology Findings | | | | | | | | | |
| Serosal Inflammation (Peritonitis) on surface of Liver | 1 | — | — | — | — | — | — | 2/6 | 1/6 |
| Liver Necrotic Focus/Foci | 1 | 2/6 | — | 1/6 | — | 1/6 | 1/6 | — | — |
| Kidneys Tubular Regeneration/Degeneration | 1 | — | — | — | 1/6 | 1/6 | 1/6 | 1/6 | — |

Key: A dash (—) indicates the absence of a finding, 1—Minimal, M—Male, F—Female

TABLE 10

Mortality Data in mice treated with a formulation combination of CBD and KML29

| Group/Dose (mg/kg) | Number of Death/Total Number of animals | |
|---|---|---|
| | Male | Female |
| I/Vehicle | 0/6 | 0/6 |
| II/0.1 mg CBD + 3 mg KML29 | 0/6 | 0/6 |
| III/0.5 mg CBD + 15 mg KML29 | 0/6 | 0/6 |
| IV/1 mg CBD + 30 mg KML29 | 0/6 | 0/6 |

TABLE 11

Summary of Clinical Signs in mice treated with a formulation combination of CBD and KML29

| Group/Dose (mg/kg) | Sex | Observations | Day - Incidence | | | | | | |
|---|---|---|---|---|---|---|---|---|---|
| | | | 1 | 2 | 3 | 4 | 5 | 6 | 7 |
| I/Vehicle | Male | NAD | 6/6 | 6/6 | 6/6 | 6/6 | 6/6 | 6/6 | 6/6 |
| | Female | NAD | 6/6 | 6/6 | 6/6 | 6/6 | 6/6 | 6/6 | 6/6 |
| II/0.1 mg CBD + 3 mg KML29 | Male | NAD | 6/6 | 6/6 | 6/6 | 6/6 | 6/6 | 6/6 | 6/6 |
| | Female | NAD | 6/6 | 6/6 | 6/6 | 6/6 | 6/6 | 6/6 | 6/6 |
| III/0.5 mg CBD + 15 mg KML29 | Male | NAD | 6/6 | 6/6 | 6/6 | 6/6 | 6/6 | 6/6 | 6/6 |
| | Female | NAD | 6/6 | 6/6 | 6/6 | 6/6 | 6/6 | 6/6 | 6/6 |
| IV/1 mg CBD + 30 mg KML29 | Male | NAD | 6/6 | 6/6 | 6/6 | 6/6 | 6/6 | 6/6 | 6/6 |
| | Female | NAD | 6/6 | 6/6 | 6/6 | 6/6 | 6/6 | 6/6 | 6/6 |

Key: NAD: No Abnormality Detected

TABLE 12

Group Mean of Body Weight in mice (n = 6) treated with a formulation combination of CBD and KML29

| Group/Dose (mg/kg) | Sex | Day & Body Weight (g)* | | | | | | | |
|---|---|---|---|---|---|---|---|---|---|
| | | −5 | 1 | 2 | 3 | 4 | 5 | 6 | 7 |
| I/Vehicle | Male | 28.14 ± 0.50 | 33.17 ± 0.85 | 33.63 ± 1.08 | 34.60 ± 1.17 | 34.86 ± 0.98 | 35.49 ± 1.12 | 35.43 ± 1.01 | 36.10 |
| | Female | 23.86 ± 0.83 | 25.79 ± 1.06 | 25.30 ± 1.08 | 25.28 ± 0.96 | 25.51 ± 0.84 | 25.67 ± 1.20 | 25.84 ± 1.44 | 26.00 ± 1.24 |
| II/0.1 mg CBD + 3 mg KML29 | Male | 28.15 ± 0.45 | 33.77 ± 0.79 | 35.47 ± 1.19 +(5) | 36.13 ± 0.61 +(4) | 36.70 ± 0.76 +(5) | 37.02 ± 0.95 | 36.60 ± 1.03 | 36.65 ± 1.11 |
| | Female | 23.89 ± 0.77 | 25.60 ± 1.29 | 25.73 ±1.33 | 26.11 ± 1.68 | 26.35 ± 1.55 | 26.52 ± 1.04 | 26.22 ± 1.52 | 26.27 ± 1.37 |
| III/0.5 mg CBD + 15 mg KML29 | Male | 28.17 ± 0.44 | 33.07 ± 0.88 | 31.25 ± 0.95 --(7) | 33.22 ± 1.11 | 34.02 ± 1.24 | 34.28 ± 1.37 | 34.73 ± 1.23 | 35.15 ± 1.42 |
| | Female | 23.82 ± 0.67 | 25.92 ± 1.26 | 25.01 ± 0.72 | 25.79 ± 0.59 | 26.50 ± 1.01 | 26.41 ± 1.33 | 26.58 ± 1.35 | 26.97 ± 1.04 |
| IV/1 mg CBD + 30 mg KML29 | Male | 28.20 ± 0.45 | 32.93 ± 1.24 | 30.77 ± 0.95 --(9) | 32.75 ± 0.91 --(5) | 33.95 ± 1.55 | 34.74 ± 1.91 | 34.62 ± 1.85 | 35.09 ± 1.94 |
| | Female | 23.85 ± 0.68 | 25.85 ± 0.88 | 24.49 ± 0.71 | 25.39 ± 1.15 | 25.72 ± 0.88 | 26.27 ± 1.02 | 26.67 ± 1.18 | 26.77 ± 1.12 |

Keys: − ($p < 0.05$) or −− ($p < 0.01$) indicates significantly lower than control group; FIG. in parenthesis indicates percent change against control.
*Mean ± S.D.

TABLE 13

Group Mean of Hematology Parameters in mice (n = 3) treated with a formulation combination of CBD and KML29

| Group/Dose (mg/kg) | Sex | Hematology Parameters* | | | | |
|---|---|---|---|---|---|---|
| | | WBC ×$10^3$ cells/μL | RBC ×$10^6$ cells/μL | HB g/dL | HCT % | MCV fL |
| I/Vehicle | M | 1.71 ± 0.28 | 9.14 ± 0.33 | 14.90 ± 0.26 | 47.50 ± 2.00 | 51.90 ± 0.53 |
| | F | 0.93 ± 0.44 | 9.13 ± 0.10 | 15.10 ± 0.26 | 47.53 ± 0.29 | 52.03 ± 0.23 |
| II/0.1 mg CBD + 3 mg KML29 | M | 1.55 ± 0.31 | 9.19 ± 0.22 | 14.73 ± 0.60 | 47.50 ± 1.11 | 51.70 ± 0.00 |
| | F | 1.35 ± 0.67 | 9.21 ± 0.45 | 15.10 ± 0.53 | 47.97 ± 1.27 | 52.13 ± 1.17 |
| III/0.5 mg CBD + 15 mg KML29 | M | 2.71 ± 0.36 | 8.83 ± 0.25 | 14.27 ± 0.51 | 46.43 ± 1.99 | 52.60 1.84 |
| | F | 2.47 ± 0.75 | 9.33 ± 0.23 | 15.07 ± 0.49 | 48.23 ± 1.61 | 51.70 ± 1.39 |
| IV/1 mg CBD + 30 mg KML29 | M | 2.56 ± 1.84 | 8.17 ± 1.38 | 13.27 ± 2.31 | 42.03 ± 8.11 | 51.27 ± 1.53 |
| | F | 1.87 ± 0.53 | 8.99 ± 0.43 | 14.77 ± 0.65 | 48.30 ± 2.43 | 53.70 ± 1.14 |

TABLE 13-continued

Group Mean of Hematology Parameters in mice (n = 3) treated with a formulation combination of CBD and KML29

| Group/Dose (mg/kg) | Hematology Parameters* | | | |
|---|---|---|---|---|
| | MCH Pg | MCHC g/dL | Reticulocytes ×10⁹ cells/L | PLT ×10³ cells/μL |
| I/Vehicle | 16.33 ± 0.32 | 31.43 ± 0.71 | 235.73 ± 43.51 | 923.33 ± 391.19 |
| | 16.57 ± 0.46 | 31.80 ± 0.78 | 322.53 ± 68.73 | 936.33 ± 61.00 |
| II/0.1 mg CBD + 3 mg KML29 | 16.03 ± 0.29 | 31.03 ± 0.55 | 180.37 ± 59.72 | 1265.33 ± 211.95 |
| | 16.40 ± 0.56 | 31.43 ± 0.58 | 211.10 ± 69.78 | 943.33 ± 151.43 |
| III/0.5 mg CBD + 15 mg KML29 | 16.23 ± 0.49 | 30.80 ± 0.26 | 266.63 ± 66.46 | 1082.67 ± 219.14 |
| | 16.17 ± 0.31 | 31.27 ± 0.25 | 239.97 ± 99.89 | 934.00 ± 108.67 |
| IV/1 mg CBD + 30 mg KML29 | 16.23 ± 0.23 | 31.70 ± 0.78 | 211.53 ± 62.28 | 880.00 ± 304.51 |
| | 16.47 ± 0.80 | 30.60 ± 0.96 | 356.07 ± 134.69 | 834.00 ± 110.77 |

Keys: −/+ ($p < 0.05$) indicates significantly higher/lower than control group;
FIGURE in parenthesis indicates percent change against control;
M—Male and F—Female
*Mean ± S.D.

TABLE 14

Group Mean of Differential Leukocytes Count in mice (n = 3) treated with a formulation combination of CBD and KML29

| Group/Dose (mg/kg) | Sex | Differential Leukocytes Count (10³ cells/uL)* | | | | |
|---|---|---|---|---|---|---|
| | | Neutrophils | Lymphocytes | Monocytes | Eosinophils | Basophils |
| I/Vehicle | Male | 0.41 ± 0.35 | 1.13 ± 0.04 | 0.02 ± 0.01 | 0.13 ± 0.14 | 0.01 ± 0.01 |
| | Female | 0.13 ± 0.06 | 0.69 ± 0.31 | 0.01 ± 0.01 | 0.10 ± 0.12 | 0.00 ± 0.00 |
| II/0.1 mg CBD + 3 mg KML29 | Male | 0.35 ± 0.27 | 1.01 ± 0.11 | 0.02 ± 0.00 | 0.16 ± 0.13 | 0.00 ± 0.01 |
| | Female | 0.14 ± 0.09 | 1.11 ± 0.57 | 0.01 ± 0.01 | 0.07 ± 0.04 | 0.00 ± 0.01 |
| III/0.5 mg CBD + 15 mg KML29 | Male | 0.82 ± 0.02 | 1.72 ± 0.32 | 0.04 ± 0.01 | 0.10 ± 0.06 | 0.01 ± 0.00 |
| | Female | 0.76 ± 0.23 ++(499) | 1.50 ± 0.47 | 0.02 ± 0.01 | 0.17 ± 0.10 | 0.01 ± 0.00 |
| IV/1 mg CBD + 30 mg KML29 | Male | 0.99 ± 0.85 | 1.23 ± 0.86 | 0.03 ± 0.02 | 0.29 ± 0.18 | 0.00 ± 0.01 |
| | Female | 0.64 ± 0.16 ++(407) | 1.14 ± 0.38 | 0.01 ± 0.01 | 0.05 ± 0.01 | 0.01 ± 0.00 |

Keys: −/+ ($p < 0.05$) or −−/++ ($p < 0.01$) indicates significantly lower/higher than control group;
Figure in parenthesis indicates percent change against control.
* Mean ± S.D.

TABLE 15

Group Mean of Clinical Chemistry Parameters in mice (n = 3) treated with a formulation combination of CBD and KML29

| Group/Dose (mg/kg) | Sex | Clinical Chemistry Parameters* | | | | |
|---|---|---|---|---|---|---|
| | | Glucose mg/dL | Total Protein g/dL | Albumin g/dL | Globulin g/dL | A/G ratio |
| I/Vehicle | Male | 219.33 ± 44.11 | 5.53 ± 0.12 | 3.37 ± 0.21 | 2.17 ± 0.21 | 1.57 ± 0.24 |
| | Female | 127.00 ± 43.31 | 5.97 ± 0.25 | 3.60 ± 0.00 | 2.37 ± 0.25 | 1.53 ± 0.17 |
| II/0.1 mg CBD + 3 mg KML29 | Male | 187.00 ± 21.93 | 5.93 ± 0.12 | 3.33 ± 0.06 | 2.60 ± 0.10 +(20) | 1.28 ± 0.06 |
| | Female | 175.33 ± 7.51 | 5.63 ± 0.42 | 3.30 ± 0.10 | 2.33 ± 0.32 | 1.43 ± 0.14 |
| III/0.5 mg CBD + 15 mg KML29 | Male | 200.33 ± 74.30 | 6.13 ± 0.21 ++(11) | 3.37 ± 0.12 | 2.77 ± 0.15 ++(28) | 1.22 ± 0.07 −(22) |
| | Female | 160.33 ± 26.08 | 5.87 ± 0.38 | 3.33 ± 0.25 | 2.53 ± 0.21 | 1.32 ± 0.12 |
| IV/1 mg 3 CBD + 0 mg KML29 | Male | 202.33 ± 20.84 | 6.03 ± 0.42 | 3.40 ± 0.20 | 2.63 ± 0.23 +(22) | 1.29 ± 0.06 |
| | Female | 207.33 ± 34.95 +(63) | 5.40 ± 0.53 | 3.27 ± 0.55 | 2.13 ± 0.35 | 1.57 ± 0.47 |

TABLE 15-continued

Group Mean of Clinical Chemistry Parameters in mice (n = 3) treated with a formulation combination of CBD and KML29

| Group/Dose (mg/kg) | Cholesterol mg/dL | Triglycerides mg/dL | HDL mg/dL | LDL mg/dL | BUN mg/dL |
|---|---|---|---|---|---|
| I/Vehicle | 149.33 ± 8.14 | 105.67 ± 33.29 | 66.70 ± 4.82 | 5.93 ± 1.29 | 14.95 ± 4.46 |
|  | 100.00 ± 23.39 | 95.33 ± 6.35 | 44.50 ± 11.64 | 5.27 ± 1.39 | 16.67 ± 1.51 |
| II/0.1 mg CBD + 3 mg KML29 | 166.67 ± 32.88 | 102.00 ± 35.54 | 77.67 ± 8.61 | 9.03 ± 4.18 | 15.73 ± 0.72 |
|  | 114.00 ± 12.49 | 103.67 ± 17.04 | 49.40 ± 7.87 | 8.53 ± 0.21 | 17.14 ± 1.35 |
| III/0.5 mg CBD + 15 mg KML29 | 170.33 ± 30.44 | 96.33 ± 23.86 | 79.77 ± 9.38 | 6.97 ± 2.64 | 16.51 ± 2.57 |
|  | 108.67 ± 40.53 | 113.00 ± 89.29 | 49.37 ± 18.41 | 5.03 ± 2.11 | 15.58 ± 0.54 |
| IV/1 mg 3 CBD + 0 mg KML29 | 170.67 ± 23.86 | 82.67 ± 6.51 | 77.57 ± 5.30 | 7.40 ± 1.64 | 16.36 ± 1.87 |
|  | 117.67 ± 10.02 | 131.33 ± 56.72 | 41.27 ± 16.11 | 6.27 ± 3.14 | 17.75 ± 3.99 |

Keys: +/− ($p < 0.05$) or ++/−− ($p < 0.01$) indicates significantly higher/lower than control group;

FIG. in parenthesis indicates percent change against control;

*Mean ± S.D.

TABLE 16

Group Mean of Clinical Chemistry Parameters in mice (n = 3) treated with a formulation combination of CBD and KML29

| Group/Dose (mg/kg) | Sex | Creatinine mg/dL | ALT U/L | AST U/L | ALP U/L | Creatine kinase U/L |
|---|---|---|---|---|---|---|
| I/Vehicle | Male | 0.52 ± 0.16** | 92.00 ± 43.00 | 125.33 ± 37.00 | 131.67 ± 17.56 | 1235.00 ± 603.58 |
|  | Female | 0.40 ± 0.14 | 50.67 ± 13.50 | 128.00 ± 43.31 | 188.67 ± 2.08 | 1263.67 ± 921.53 |
| II/0.1 mg CBD + 3 mg KML29 | Male | 0.57 ± 0.09 | 84.33 ± 71.60 | 118.33 ± 47.86 | 145.33 ± 1.53 | 772.00 ± 252.37 |
|  | Female | 0.60 ± 0.12 | 48.33 ± 13.20 | 151.67 ± 32.13 | 150.33 ± 24.17 −(20) | 1148.50 ± 321.73** |
| III/0.5 mg CBD + 15 mg KML29 | Male | 0.54 ± 0.16 | 83.67 ± 44.47 | 89.00 ± 21.38 | 108.67 ± 31.09 | 293.33 ± 89.90 −(76) |
|  | Female | 0.91 ± 0.77** | 52.33 ± 18.90 | 120.33 ± 30.04 | 135.00 ± 9.64± −−(28) | 590.00 ± 356.13 |
| IV/1 mg CBD + 30 mg KML29 | Male | 0.61 ± 0.18 | 75.33 ± 24.83 | 76.00 ± 23.43 | 85.67 ± 18.01 | 360.33 ± 240.25 −(71) |
|  | Female | 0.50*** | 70.33 ± 15.95 | 90.67 ± 20.53 | 109.67 ± 17.21 −−(42) | 303.00 ± 127.40 |

| Group/Dose (mg/kg) | Calcium mg/dL | Magnesium mg/dL | Phosphorous mg/dL | GGT U/L | Total Bilirubin mg/dL |
|---|---|---|---|---|---|
| I/Vehicle | 10.51 ± 0.55 | 2.64 ± 0.29 | 11.61 ± 0.25 | — | — |
|  | 10.55 ± 0.20 | 2.37 ± 0.04 | 10.25 ± 0.53 | — | 0.15*** |
| II/0.1 mg CBD + 3 mg KML29 | 10.67 ± 0.42 | 2.57 ± 0.20 | 11.39 ± 1.13 | — | — |
|  | 10.54 ± 0.10 | 2.65 ± 0.00 | 11.36 ± 1.16 | — | — |
| III/0.5 mg CBD + 15 mg KML29 | 11.19 ± 0.46 | 2.56 ± 0.20 | 11.73 ± 0.50 | — | — |
|  | 10.65 ± 0.14 | 2.54 ± 0.31 | 11.70 ± 1.12 | — | — |

TABLE 16-continued

Group Mean of Clinical Chemistry Parameters in mice (n = 3) treated with a formulation combination of CBD and KML29

| | | | | | |
|---|---|---|---|---|---|
| IV/1 mg CBD + 30 mg KML29 | 11.16 ± 0.54 9.88 ± 1.72 | 2.32 ± 0.27 2.96 ± 0.49 | 11.05 ± 0.27 8.15 ± 0.39 −(20) | — — | — — |

Keys: +/− ($p < 0.05$) indicates significantly higher/lower than control group; FIG. in parenthesis indicates percent change against control; a (—) indicates the values were below lower limit of quantification.

\* Mean ± S.D.

\*\*n = 2

\*\*\*n = 1

TABLE 17

Group Mean of Clinical Chemistry Parameters in mice (n = 3) treated with a formulation combination of CBD and KML29

| Group/Dose (mg/kg) | Sex | Sodium mmol/L | Potassium mmol/L | Chloride mmol/L |
|---|---|---|---|---|
| I/Vehicle | Male | 154.35 ± 2.04 | 4.85 ± 0.88 | 116.04 ± 2.21 |
| | Female | 152.94 ± 1.63 | 4.78 ± 0.37 | 113.82 ± 1.91 |
| II/0.1 mg CBD + 3 mg KML29 | Male | 156.78 ± 3.71 | 4.22 ± 0.22 | 113.55 ± 2.18 |
| | Female | 156.97 ± 9.40 | 5.58 ± 1.20 | 113.58 ± 4.96 |
| III/0.5 mg CBD + 15 mg KML29 | Male | 152.73 ± 3.73 | 5.62 ± 0.68 | 113.27 ± 0.47 |
| | Female | 158.50 ± 10.90 | 5.20 ± 1.03 | 115.80 ± 6.04 |
| IV/1 mg CBD + 30 mg KML29 | Male | 150.99 ± 4.42\*\* | 4.90 ± 0.17\*\* | 112.32 ± 0.57\*\* |
| | Female | 152.70 ± 1.22 | 5.04 ± 1.59 | 113.01 ± 2.65 |

\*Mean ± S.D.

\*\*n = 2

TABLE 18

Summary of Urinalysis in mice treated with a formulation combination of CBD and KML29

| Parameter | Group Dose (mg/kg) Sex | I/Vehicle Male | I/Vehicle Female | II II/0.1 mg CBD + 3 mg KML29 Male | II II/0.1 mg CBD + 3 mg KML29 Female |
|---|---|---|---|---|---|
| Volume (μL) | Mean ± S.D. | 266.67 ± 172.24 | 173.33 ± 127.54 | 185.00 ± 113.45 | 203.33 ± 153.19 |
| Protein (mg/dL) | Negative | — | 1/6 | — | 1/6 |
| | Trace | — | 2/6 | 1/6 | 4/6 |
| | 30 | 5/6 | 3/6 | 3/6 | 1/6 |
| | 100 | 1/6 | — | 2/6 | — |
| | Yellow | — | — | — | 2/6 |
| Color | Pale Yellow | 6/6 | 6/6 | 6/6 | 4/6 |
| Clarity | Clear | 6/6 | 6/6 | 6/6 | 6/6 |
| Glucose (mg/dL) | Negative | 5/6 | 6/6 | 6/6 | 6/6 |
| | 100 | 1/6 | — | — | — |
| Bilirubin | Negative | 6/6 | 6/6 | 6/6 | 6/6 |
| Ketone (mg/dL) | Negative | 2/6 | — | 2/6 | 4/6 |
| | Trace | 1/6 | 5/6 | 4/6 | 2/6 |
| | 15 | 3/6 | 1/6 | — | — |
| Specific Gravity | Mean ± S.D. | 1.020 ± 0.004 | 1.018 ± 0.003 | 1.019 ± 0.005 | 1.019 ± 0.005 |
| Blood | Negative | 6/6 | 6/6 | 6/6 | 5/6 |
| | Trace Intact | — | — | — | 1/6 |
| pH | Mean ± S.D. | 7.33 ± 0.41 | 7.83 ± 0.61 | 7.50 ± 0.77 | 7.08 ± 0.38 |
| Urobilinogen (EU/dL) | 0.20 | 6/6 | 6/6 | 6/6 | 6/6 |
| Nitrite | Negative | 6/6 | 6/6 | 6/6 | 6/6 |
| Leukocyte | Negative | 6/6 | 4/6 | 6/6 | 6/6 |
| | Trace | — | 2/6 | — | — |

TABLE 18-continued

Summary of Urinalysis in mice treated with a formulation combination of CBD and KML29

| | | III | | IV | |
| | | III/0.5 mg CBD + 15 mg KML29 | | IV/1 mg CBD + 30 mg KML29 | |
| Parameter | | Male | Female | Male | Female |
| --- | --- | --- | --- | --- | --- |
| Volume (μL) | | 233.33 ± 137.21 | 158.33 ± 46.65 | 296.67 ± 163.30 | 30.00 ± 138.62 |
| Protein | | 1/6 | 2/6 | — | — |
| (mg/dL) | | 2/6 | 3/6 | 3/6 | 3/6 |
| | | 3/6 | 1/6 | 3/6 | 3/6 |
| | | — | — | — | — |
| | | — | — | — | — |
| Color | | 6/6 | 6/6 | 6/6 | 6/6 |
| Clarity | | 6/6 | 6/6 | 6/6 | 6/6 |
| Glucose | | 6/6 | 6/6 | 6/6 | 6/6 |
| (mg/dL) | | — | — | — | — |
| Bilirubin | | 6/6 | 6/6 | 6/6 | 6/6 |
| Ketone | | 5/6 | 4/6 | 5/6 | 3/6 |
| (mg/dL) | | — | 2/6 | — | 2/6 |
| | | 1/6 | — | 1/6 | 1/6 |
| Specific Gravity | | 1.018 ± 0.004 | 1.016 ± 0.004 | 1.015 ± 0.004 | ± 0.004 |
| Blood | | 5/6 | 6/6 | 6/6 | 5/6 |
| | | 1/5 | — | — | 1/6 |
| pH | | 7.67 ± 0.52 | 7.70 ± 0.91 | 7.33 ± 0.61 | 7.17 ± 0.68 |
| Urobilinogen (EU/dL) | | 6/6 | 6/6 | 6/6 | 6/6 |
| Nitrite | | 6/6 | 6/6 | 6/6 | 6/6 |
| Leukocyte | | 5/6 | 5/6 | 4/6 | 6/6 |
| | | 1/6 | 1/6 | 2/6 | — |

Keys: A dash (—) indicates the absence of finding in the group, Value indicates the number of incidences except for urine volume, protein, specific gravity, and pH.

TABLE 19

Group Mean of Relative Organ Weight in mice (n = 6) treated with a formulation combination of CBD and KML29

| Group/Dose (mg/kg) | Sex | Mean Body Weight | Relative Organ Weight (%) | | | | | |
| --- | --- | --- | --- | --- | --- | --- | --- | --- |
| | | | Liver | Kidneys | Heart | Brain | Spleen | Lung |
| I/Vehicle | Male | 33.80 ± 1.13 | 5.6584 ± 0.31 | 1.5720 ± 0.10 | 0.5446 ± 0.02 | 1.6371 ± 0.11 | 0.3498 ± 0.05 | 0.6242 ± 0.08 |
| | Female | 24.05 ± 1.15 | 5.2664 ± 0.40 | 1.3831 ± 0.08 | 0.5999 ± 0.04 | 2.2021 ± 0.05 | 0.4101 ± 0.04 | 0.8155 ± 0.07 |
| II/0.1 mg CBD + 3 mg KML29 | Male | 34.21 ± 0.88 | 5.5085 ± 0.49 | 1.4656 ± 0.13 | 0.5165 ± 0.04 | 1.5174 ± 0.07 | 0.3021 ± 0.07 | 0.6998 ± 0.09 |
| | Female | 24.36 ± 1.44 | 5.4182 ± 0.38 | 1.3347 ± 0.14 | 0.5907 ± 0.05 | 2.1086 ± 0.15 | 0.4062 ± 0.08 | 0.8190 ± 0.06 |
| III/0.5 mg CBD + 15 mg KML29 | Male | 32.59 ± 1.32 | 6.0094 ± 0.33 | 1.6442 ± 0.20 | 0.5542 ± 0.02 | 1.5798 ± 0.09 | 0.3731 ± 0.05 | 0.7278 ± 0.07 |
| | Female | 24.65 ± 0.90 | 5.7591 ± 0.33 | 1.3742 ± 0.15 | 0.6133 ± 0.09 | 2.2358 ± 0.13 | 0.6146 ± 0.13 ++ (50) | 0.8599 ± 0.14 |
| IV/1 mg CBD + 30 mg KML29 | Male | 32.80 ± 1.93 | 6.1488 ± 0.73 | 1.7302 ± 0.24 | 0.5359 ± 0.04 | 1.6069 ± 0.06 | 0.4955 ± 0.10 ++ (42) | 0.7147 ± 0.07 |
| | Female | 24.3100 ± 1.28 | 5.8174 ± 0.31 | 1.3523 ± 0.11 | 0.6000 ± 0.03 | 2.1627 ± 0.16 | 0.4886 ± 0.07 | 0.7878 ± 0.12 |

Keys: —/++ (p < 0.01) indicates significantly lower/higher than control group;
FIG. in parenthesis indicates percent change against control

TABLE 20

Summary of Gross Pathological Findings in mice treated with a formulation combination of CBD and KML29

| Group | I | II | III | IV |
|---|---|---|---|---|
| Dose (mg/kg) | I/Vehicle | II/0.1 gm CBD + 3 mg KML29 | III/0.5 mg CBD + 15 mg KML29 | IV/1 mg CBD + 30 mg KML29 |
| Mode of Sacrifice | TS | TS | TS | TS |
| Necropsy findings | \multicolumn{4}{c}{Incidence (No. of animals with findings/No. of animals examined)} | | | |

Sex: Male

| | | | | |
|---|---|---|---|---|
| NAD | 6/6 | 6/6 | 6/6 | — |
| Spleen: Whitish Deposits | — | — | — | 6/6 |

Sex: Female

| | | | | |
|---|---|---|---|---|
| NAD | 6/6 | 6/6 | 6/6 | — |
| Spleen: Whitish Deposits | — | — | — | 6/6 |

Keys: NAD—No Abnormality Detected, TS—Terminal Sacrifice, A dash (—) indicates the absence of findings.

TABLE 21

Summary of Histopathology Finding in mice treated with a formulation combination of CBD and KML29

| | | Group | | | | | | |
|---|---|---|---|---|---|---|---|---|
| | | I | | II | | III | | IV |
| | | \multicolumn{8}{c}{Dose (mg/kg)} | | | | | | | |
| | | 0 mg/kg (Vehicle) | | 0.1 mg/kg CBD + 3 mg/kg KML29 | | 0.5 mg/kg CBD + 15 mg/kg KML29 | | 1.0 mg/kg CBD + 30 mg/kg KML29 |
| Sex | Severity | Male | Female | Male | Female | Male | Female | Male | Female |
| Number of animals examined | | 6 | 6 | 6 | 6 | 6 | 6 | 6 | 6 |
| \multicolumn{10}{c}{Histopathology Findings} | | | | | | | | | |
| Serosal Inflammation (Peritonitis) on surface of Liver | Minimal | — | — | — | — | 5/6 | 5/6 | 5/6 | 2/6 |
| | Slight | — | — | — | — | — | 1/6 | — | 3/6 |
| Kidneys | Minimal | — | — | — | — | 4/6 | 5/6 | 5/6 | 5/6 |
| Spleen | Minimal Slight | — | — | — | — | 4/6 | 6/6 | 6/6 | 5/6 |
| \multicolumn{10}{c}{Liver} | | | | | | | | | |
| Necrotic Focus/Foci | Minimal | 3/6 | — | 1/6 | 2/6 | 1/6 | — | 3/6 | 1/6 |
| Microvesicular Vacuolation | Minimal | 1/6 | — | — | — | — | — | — | — |
| Neutrophilic Infiltration | Minimal | — | — | — | — | — | — | — | 1/6 |
| \multicolumn{10}{c}{Kidneys} | | | | | | | | | |
| Tubular Regeneration/Degeneration | Minimal | 1/6 | 2/6 | — | — | 2/6 | 1/6 | 1/6 | 1/6 |
| | Slight | — | — | 1/6 | — | — | — | — | — |
| Cyst | Minimal | — | — | — | — | 1/6 | — | — | — |
| Pyelitis | Minimal | — | — | — | — | — | — | 1/6 | — |
| \multicolumn{10}{c}{Heart} | | | | | | | | | |
| Vacuolar Degeneration | Minimal | — | — | — | 1/6 | — | — | — | — |
| \multicolumn{10}{c}{Lung} | | | | | | | | | |
| Neutrophilic Infiltration | Minimal | 1/6 | — | — | — | — | — | — | — |

Key: A dash (—) indicates the absence of a finding.

Detection of Synergistic Effects

The interactive effect of the combination of (a) KML29 and CBD, and (b) JZL184 and CBD was detected by comparing the level of response of the mice to KML29 alone or JZL184 alone, cannabidiol alone, and the two combined. If the CBD+MAGL inhibitor treated groups demonstrate greater than an additive effect of the CBD, and MAGL inhibitor individually for a particular concentration, then synergism is observed.

Figure 3:
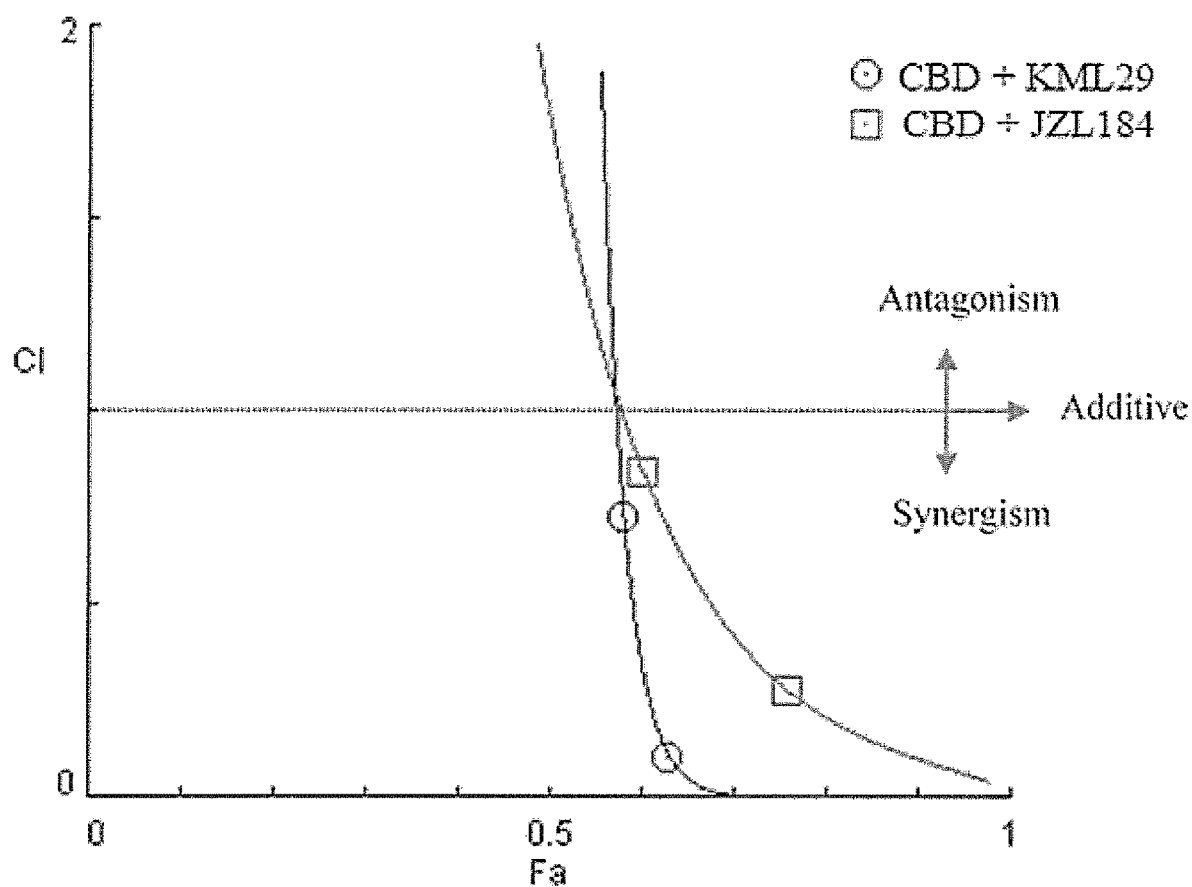
FIG. 3 shows a combination Index (CI) plot determining synergistic effect of drug combinations.

The data is presented in FIG. 3. The drug combination is considered synergism if CI<1, antagonism if CI>1, and additive effect if CI=1. The two-drug combination CBD+KML29 and CBD+JZL184 appeared synergistic at all tested concentrations, indicating that the multiple mechanisms of action enhanced the potency of the combination than the individual drug treatments alone. CI value for the combined total dose of CBD (0.1 mg/kg)+KML29 (3 mg/kg) was 0.108; CBD (1 mg/kg)+KML29 (30 mg/kg) was 0.729; CBD (0.1 mg/kg)+JZL184 (3 mg/kg) was 0.76; and CBD (0.1 mg/kg)+JZL184 (3 mg/kg) was 0.60.

Preparation of Formulation

The benzodiazepine diazepam (greater than 99%) was provided by known active pharmaceutical ingredient suppliers (e.g. R&D System, Inc.). The MAGL inhibitors KML29 and JZL184 (Purity, >98%) was provided by known active pharmaceutical ingredient suppliers (e.g. Cayman chemicals)

Excipients and stabilizers were purchased from known commercial suppliers, such as BASF Canada, Rouquette Pharma or Cayman Chemical Co. The excipients and stabilizers ensure the active pharmaceutical ingredients are mixed and stabilized to optimize product shelf life and to ensure high-quality assurance and quality control of product to the highest standards of good manufacturing practices for pharmaceutical products. Not every advantage implied by each of these elements is necessary for the use of the invention.

The ingredients were mixed in a uniform manner to meet all quality assurance and quality control standards of good manufacturing practices for pharmaceutical products using methods known in the scientific art and as described for example below.

The formulation may be in a tablet form that contains between 1 mg and 1000 mg of CBD as of human equivalent dose (HED), and 0.1 to 500 mg of MAGL inhibitor as of HED as active pharmaceutical ingredients. These active pharmaceutical ingredients may be blended with the necessary excipients and stabilizers to ensure optimized product shelf life and consistency of dose. The dosage range for CBD may be between 0.1-150 mg/kg body weight. The dosage range for MAGL inhibitor may be between 0.1-150 mg/kg body weight. The dosage range for the formulation comprising MAGL inhibitor and CBD may be between 0.1-150 mg/kg JZL184 and KML29, and between 0.1-150 mg/kg for CBD.

Other embodiments are aerosols, liquids, or patches which may deliver similar doses of active pharmaceutical ingredients to the patient.

An example of the product formulation includes a nanoemulsion forming composition (% w/w) for transmucosal delivery of medication was prepared as described in WO 2014127458 A1 [21]. In brief:

The vehicle may be prepared by dissolving acetylated monoglycerides (45%), containing lecithin and alcohol (6.5% of each), D-alpha-Tocopherol (2%), Polysorbate-20 (18%) and polyethoxylated hydrogenated castor oil (22%). CBD and MAGL inhibitor (dose to be determined from preclinical and pilot studies) was dissolved in the vehicle at 40° C., sealed, and stored under dark conditions in a refrigerator.

Another example of the product formulation includes a capsule forming composition (% w/w of the capsule) for oral delivery was prepared as described in WO 2013098402 A1 [22] [23]. In brief:

Step 1: Anhydrous lactose (28.0%), MAGL inhibitor (dose to be determined from preclinical and pilot studies 0.01 mg and 1000 mg) and a part (3.925%) of polyvinyl N-pyrrolidone (PVP) was mixed and sieved through a suitable sieve. To this mixture, fine Sodium Stearyl Fumarate (1.25%) may be added. Tablets may be compressed with suitable punches.

Step 2: CBD (dose—determined from preclinical, 1 mg and 1000 mg), pre-gelatinized starch (6.25%), MAGL inhibitors (Human equivalent dose determined from preclinical between 0.1 mg to 500 mg) and the remaining part of PVP (5.0%) was mixed homogeneously. This powdery mixture may be added to microcrystalline cellulose (Avicel PH 102) (23.75%) to obtain CBD granules.

Step 3: Both MAGL inhibitor tablets (step 1) and CBD granules (step 2) may be filled into hard gelatin capsule using Zanasi 40E Capsule Filling Machine.

Another example of the product formulation includes a double layer tablet forming composition (% w/w of the tablet) for oral delivery was prepared as described in WO 2013098402 A1 [22]. In brief:

Step 1: MAGL inhibitor (dose determined from preclinical and pilot studies), 0.01 mg and 1000 mg) and a portion of mannitol (10.0%) was dry mixed with PVP (2.0%). To this mixture, mannitol (12.25%), microcrystalline cellulose (19.0%) and croscamellose sodium (6.0%) were added and mixed. Finally, Magnesium Stearate (0.5%) was added, mixed, and the tablet layer were pressed using a tablet pressing machine.

Step 2: For the preparation of CBD layer, CBD (dose may be determined from preclinical and pilot studies, 1 mg and 1000 mg), and poloxamer 188 (6.0%) was mixed and passed through a suitable sieve. To this mixture, mannitol (6.0%), microcrystalline cellulose (2.8%) and PVP (3.0%) were added and passed through a suitable sieve. Finally, magnesium stearate (0.5%) was added and mixed. This resulting mixture was ready for compression.

Step 3: Double layer tablets was compressed from prepared MAGL inhibitor layer (step 1) and CBD layer (step 2) using Fette 102i Tablet Press Machine.

REFERENCES

1. *Handbook of Cannabis.* 2014, Oxford: Oxford University Press. 784.
2. Huestis, M. A., *Human cannabinoid pharmacokinetics.* Chem Biodivers, 2007. 4(8): p. 1770-804.
3. Zuardi, A. W., *Cannabidiol: from an inactive cannabinoid to a drug with wide spectrum of action.* Braz J Psychiatr, 2008. 30(3): p. 271-80.
4. Zuardi, A. W., et al., *Effects of ipsapirone and cannabidiol on human experimental anxiety.* J Psychopharmacol, 1993. 7(1 Suppl): p. 82-8.
5. Cunha, J. M., et al., *Chronic administration of cannabidiol to healthy volunteers and epileptic patients.* Pharmacology, 1980. 21(3): p. 175-85.
6. Consroe, P., et al., *Controlled clinical trial of cannabidiol in Huntington's disease.* Pharmacol Biochem Behav, 1991. 40(3): p. 701-8.
7. Karlsson, M., et al., *cDNA Cloning, Tissue Distribution, and Identification of the Catalytic Triad of Monoglyceride Lipase.* Journal of Biological Chemistry, 1997. 272(43): p. 27218-27223.
8. WO02/064109, *Extraction of pharmaceutically active cannabinoids from plant materials*, in European publication server.
9. WO2002032420A1, *Method for producing an extract from cannabis plant matter, containing a tetrahydrocannabinol and a cannabidiol and cannabis extracts.* 2002.
10. Repetto, M., Lopez-Artiguez, M., Martinez, D., *Separation of cannabinoids.* United Nations Office on Drugs and Crime (UNODC), 1976.
11. Narayanaswami K., G. H. C., Bam H.1, *Stability of Cannabis sativa L. samples and their extracts, on prolonged storage in Delhi.* United Nations Office on Drugs and Crime (UNODC), 1978.
12. Smith, R. N. and C. G. Vaughan, *The decomposition of acidic and neutral cannabinoids in organic solvents.* Journal of Pharmacy and Pharmacology, 1977. 29(1): p. 286-290.
13. U.S. Pat. No. 7,700,368B2, *Methods of purifying cannabinoids from plant material*, U.S. Patent, Editor.
14. WO2004026802A1, *Method of preparing cannabidiol from plant material*, W.I.P. Organization, Editor.
15. Aubin, A., *Purification of Cannabidiol from Hemp Oil Using the Prep150 LC System. Water Application Notes*, in http://www.waters.com/waters/webassets. 2015.
16. Bachovchin, D. A. and B. F. Cravatt, *The pharmacological landscape and therapeutic potential of serine hydrolases.* Nat Rev Drug Discov, 2012. 11(1): p. 52-68.
17. Chou, T. C., Martin, N., *CompuSyn for drug combinations: PC software and user's guide, A Computer Program for Quantitation of Synergism and Antagonism in*

*Drug Combinations, and the Determination of IC50 and ED50 and LD50 Values*. CompuSyn, PD Science. 2005, Paramus, N.J. 7652-1754.
18. Fu, J., et al., *Drug combination in vivo using combination index method: Taxotere and T607 against colon carcinoma HCT-116 xenograft tumor in nude mice*. 2016. 3(3): p. 15-30.
19. Remington, J. P. and A. R. Gennaro, *Remington's pharmaceutical sciences*. 1990, Easton, Pa.: Mack Pub. Co.
20. Tiwari P, et al., *Phytochemical screening and Extraction: A Review*. Internationale Pharmaceutica Sciencia, 2011. 1(1): p. 100-106.
21. WO2014127458A1, *Pharmaceutical composition for transmucosal administration of benzodiazepines*, W.I.P. Organization, Editor. 2014.
22. WO2013098402A1, *Pharmaceutical combination of fingolimod and nabiximols*, W.I.P. Organization, Editor. 2013: Istanbul.

All citations are hereby incorporated by reference.

The present invention has been described with reference to one or more embodiments. However, it will be apparent to persons skilled in the art that several variations and modifications can be made without departing from the scope of the invention as defined in the claims.

What is claimed is:

1. A formulation for treating an affective disorder consisting of a combination of
   i) an effective amount of one or more than one cannabinoid; and
   ii) an effective amount of one or more than one monoacylglycerol lipase (MAGL) inhibitor, wherein the MAGL inhibitor is KML29, JZL184, or a combination thereof.

2. The formulation of claim 1, wherein the combination of the one or more than one cannabinoid, and the one or more than one MAGL inhibitor comprises a drug combination index (CI) of <1, when determined with the Chou-Talalay combination index method.

3. The formulation of claim 1, wherein the one or more than one cannabinoid is an anxiolytic cannabinoid.

4. The formulation of claim 1, where the one or more than one cannabinoid is cannabidiol (CBD).

5. The formulation of claim 1, wherein the affective disorder comprises anxiety disorders.

6. The formulation of claim 5, wherein the anxiety disorders comprise generalized anxiety disorder, phobias, panic disorder, panic attacks, obsessive-compulsive disorder (OSD), post-traumatic stress disorder (PTSD), separation anxiety disorder, situational anxiety disorder, stress or a combination thereof.

7. The formulation of claim 1, wherein the one or more than one cannabinoid and the one or more than one MAGL inhibitor is present in an effective amount to improve the therapeutic outcome and reduced dosage of the one or more than one cannabinoid and/or one or more than one MAGL inhibitor.

8. The formulation of claim 4, wherein the effective amount of CBD is between 0.01 mg and 1000 mg.

9. The formulation of claim 1, wherein the effective amount of the one or more MAGL inhibitor is between 0.01 mg and 1000 mg.

10. A pharmaceutical preparation for treating affective disorder comprising the formulation of claim 1 and a physiologically acceptable surface-active agents, carriers, diluents, excipients, smoothing agents, suspension agents, film forming substances, and coating assistants, or a combination thereof.

11. A method of treating an affective disorder by administering to a subject in need thereof the formulation of claim 1.

12. The method of claim 11, wherein the treating comprises an extended treatment period.

13. The method of claim 12, wherein the extended treatment period is at least 21 days.

14. The method of claim 11, wherein the treating comprises a protracted treatment period.

15. The method of claim 14, wherein the protracted treatment period comprises between about 1 to about 21 days or any amount of days therebetween.

16. The method of claim 1, wherein the formulation is administered transmucosally, parenterally or orally.

17. The method of claim 16, wherein transmucosal administration is sublingual, buccal, nasal, ocular, vaginal, and/or rectal mucosae.

18. The method of claim 11, wherein the formulation is delivered in an appropriate aerosol, liquid, gel, film, or tablet/solid drug carrier with drug stabilizers/additives.

19. The method of claim 11, wherein the affective disorder comprises anxiety.

20. The method of claim 19, wherein the anxiety comprises generalized anxiety disorder, phobias, panic disorder, panic attacks, obsessive-compulsive disorder, post-traumatic stress disorder (PTSD), separation anxiety disorder, situational anxiety disorder, stress or a combination thereof.

21. A method of treating an affective disorder by administering to a subject in need thereof the pharmaceutical preparation of claim 10.

* * * * *